US010220392B2

(12) United States Patent
Baum et al.

(10) Patent No.: US 10,220,392 B2
(45) Date of Patent: Mar. 5, 2019

(54) PROCESS TUBE AND CARRIER TRAY

(71) Applicant: BECTON, DICKINSON AND COMPANY, Franklin Lakes, NJ (US)

(72) Inventors: Michael J. Baum, Fallston, MD (US); Brent Pohl, Timonium, MD (US); Ed Belsinger, Forest Hill, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 14/844,936

(22) Filed: Sep. 3, 2015

(65) Prior Publication Data

US 2015/0376562 A1 Dec. 31, 2015

Related U.S. Application Data

(63) Continuation of application No. PCT/US2013/032556, filed on Mar. 15, 2013.

(51) Int. Cl.
*C12M 1/12* (2006.01)
*B01L 9/06* (2006.01)
*B01L 3/00* (2006.01)

(52) U.S. Cl.
CPC ............ *B01L 9/06* (2013.01); *B01L 3/50855* (2013.01); *B01L 3/527* (2013.01); *B01L 2200/025* (2013.01); *B01L 2200/12* (2013.01); *B01L 2200/18* (2013.01); *B01L 2300/0829* (2013.01); *B01L 2300/0851* (2013.01); *B01L 2300/0858* (2013.01)

(58) Field of Classification Search
CPC ............................ B01L 9/523; B01L 3/50855
See application file for complete search history.

(56) References Cited

U.S. PATENT DOCUMENTS

D229,748 S 1/1974 White
4,956,150 A 9/1990 Henry
5,141,718 A * 8/1992 Clark ................. B01L 3/50255 422/501
D342,793 S 12/1993 Balmer
(Continued)

FOREIGN PATENT DOCUMENTS

CN 201316627 Y 9/2009
EP 0483620 A2 5/1992
(Continued)

OTHER PUBLICATIONS

International Search Report and Written Opinion dated Jan. 28, 2014 for International Application No. PCT/US2013/032556.
(Continued)

*Primary Examiner* — Kathryn Wright
(74) *Attorney, Agent, or Firm* — Knobbe Martens Olson & Bear LLP

(57) ABSTRACT

The disclosure provides a system and method to safely and efficiently store and transport process tubes in a carrier tray comprising prior to and during amplification of nucleotides in the process tubes. The process tube disclosed includes a securement region having an annular ledge, a neck, and a protrusion. The securement region of the process tube can secure the process tube in a port of the carrier tray, but still allows the process tube to adjust or float in order to align the process tube into a rigid heater well of a thermal cycler.

14 Claims, 16 Drawing Sheets

(56) References Cited

U.S. PATENT DOCUMENTS

| | | | |
|---|---|---|---|
| 5,462,881 A | 10/1995 | Perlman | |
| D367,932 S | 3/1996 | Lim | |
| D380,555 S | 7/1997 | Kurosaki et al. | |
| 5,683,659 A | 11/1997 | Hovatter | |
| 5,721,136 A | 2/1998 | Finney et al. | |
| 5,753,186 A | 5/1998 | Hanley et al. | |
| 5,762,874 A | 6/1998 | Seaton et al. | |
| D401,700 S | 11/1998 | Gray et al. | |
| 5,922,289 A * | 7/1999 | Wong | B01L 3/5085 422/553 |
| 5,948,363 A | 9/1999 | Gaillard | |
| 6,027,694 A | 2/2000 | Boulton et al. | |
| 6,117,391 A | 9/2000 | Mootz et al. | |
| D445,907 S | 7/2001 | Monks | |
| D453,573 S | 2/2002 | Lafond et al. | |
| 6,602,206 B1 | 8/2003 | Niermann et al. | |
| 6,672,458 B2 | 1/2004 | Hansen et al. | |
| D511,214 S | 11/2005 | Sasano et al. | |
| D583,481 S | 12/2008 | Yamamoto et al. | |
| D605,303 S | 12/2009 | Monks | |
| D608,013 S | 1/2010 | Coulling et al. | |
| D624,659 S | 9/2010 | Nuotio | |
| 8,216,530 B2 | 7/2012 | Handique et al. | |
| D679,830 S | 4/2013 | May et al. | |
| D684,703 S | 6/2013 | Watzele et al. | |
| D687,567 S | 8/2013 | Jungheim et al. | |
| D687,964 S | 8/2013 | Trump | |
| D687,965 S | 8/2013 | Trump | |
| D703,345 S | 4/2014 | Tajima et al. | |
| D709,624 S | 7/2014 | Baum et al. | |
| D709,625 S | 7/2014 | Baum et al. | |
| D717,468 S | 11/2014 | Tsai | |
| 9,051,604 B2 | 6/2015 | Handique | |
| D742,027 S | 10/2015 | Lentz et al. | |
| 9,186,677 B2 | 11/2015 | Williams et al. | |
| D759,835 S | 6/2016 | Baum et al. | |
| D762,873 S | 8/2016 | Baum et al. | |
| 2001/0005489 A1 | 6/2001 | Roach et al. | |
| 2001/0016358 A1 | 8/2001 | Osawa et al. | |
| 2002/0131903 A1 | 9/2002 | Ingenhoven et al. | |
| 2003/0059823 A1 | 3/2003 | Matsunaga et al. | |
| 2005/0058578 A1* | 3/2005 | Guelzow | B01L 3/5085 422/553 |
| 2005/0064535 A1 | 3/2005 | Favuzzi et al. | |
| 2006/0205085 A1 | 9/2006 | Handique | |
| 2007/0077648 A1 | 4/2007 | Okamoto et al. | |
| 2007/0116613 A1 | 5/2007 | Elsener | |
| 2008/0023423 A1* | 1/2008 | Duffy | A47B 73/004 211/85.18 |
| 2008/0287585 A1 | 11/2008 | Brown | |
| 2009/0047180 A1 | 2/2009 | Kawahara | |
| 2010/0284864 A1 | 11/2010 | Holenstein et al. | |
| 2012/0129250 A1 | 5/2012 | Seippel | |
| 2013/0029343 A1 | 1/2013 | Day et al. | |
| 2014/0271409 A1 | 9/2014 | Knight et al. | |
| 2015/0315631 A1 | 11/2015 | Handique et al. | |
| 2015/0328638 A1 | 11/2015 | Handique et al. | |

FOREIGN PATENT DOCUMENTS

| | | | |
|---|---|---|---|
| EP | 0688602 | A2 | 12/1995 |
| EP | 1077086 | A2 | 2/2001 |
| EP | 1346772 | A2 | 9/2003 |
| EP | 1792656 | A1 | 6/2007 |
| GB | 2453432 | A | 4/2009 |
| JP | H08-337116 | A | 12/1996 |
| JP | H10-327515 | A | 12/1998 |
| JP | 2007-155717 | A2 | 6/2007 |
| WO | WO 1998/35013 | A1 | 8/1998 |
| WO | WO 2004/056485 | A1 | 7/2004 |
| WO | WO 2005/108571 | | 11/2005 |
| WO | WO 2006/043642 | | 4/2006 |
| WO | WO 2011/101467 | | 8/2011 |

OTHER PUBLICATIONS

International Written Opinion (PCT Rule 66) dated Apr. 8, 2015 for International Application No. PCT/US2013/032556.

International Preliminary Report on Patentability dated Jul. 3, 2015 for International Application No. PCT/US2013/032556.

* cited by examiner

PROCESS TUBE AND CARRIER TRAY

CROSS-REFERENCE TO RELATED APPLICATIONS

This application is a continuation of International Patent Application No. PCT/US2013/032556, filed Mar. 15, 2013, entitled "PROCESS TUBE AND CARRIER TRAY," the entire disclosure of which is hereby incorporated by reference in its entirety.

BACKGROUND

Field of the Development

The technology described herein generally relates to process tubes used in amplification processes and the carrier trays in which the process tubes are securely stored for transport and processing, as well as methods of making and using the same.

Description of the Related Art

The medical diagnostics industry is a critical element of today's healthcare infrastructure. At present, however, in vitro diagnostic analyses, no matter how routine, have become a bottleneck in patient care. Understanding that diagnostic assays of biological samples may break down into several key steps, it is often desirable to automate one or more steps. For example, a biological sample, such as those obtained from a patient, can be used in nucleic acid amplification assays, in order to amplify a target nucleic acid (e.g., DNA, RNA, or the like) of interest. Polymerase chain reaction (PCR), conducted in a thermal cycler device, is one such amplification assay used to amplify a sample of interest.

Once amplified, the presence of a target nucleic acid, or amplification product of a target nucleic acid (e.g., a target amplicon) can be detected, wherein the presence of a target nucleic acid and/or target amplicon is used to identify and/or quantify the presence of a target (e.g., a target pathogen, genetic mutation or alteration, or the like). Often, nucleic acid amplification assays involve multiple steps, which can include nucleic acid extraction and preparation, nucleic acid amplification, and target nucleic acid detection.

In many nucleic acid-based diagnostic assays, the biological, environmental, or other samples to be analyzed, once obtained, are mixed with reagents for processing. Such processing can include combining extracted nucleic acids from the biological sample with amplification and detection reagents, such as probes and fluorophores. Processing samples for amplification is currently a time-consuming and labor intensive step.

Processing samples for amplification often occurs in dedicated process tubes, used to hold the extracted DNA samples prior to and during the amplification process. In some instances, the process tubes are placed directly in a thermal cycler for amplification. In some instances, to simplify the procedure, process tubes are first placed in a tube rack for pre-amplification processing (such as filling up the tubes with the amplification reagents, drying the reagents, and marking the tubes by hot stamping them). The process tubes are often removed from the tube rack by a lab technician and placed individually and separately in contact with a heater unit of the thermal cycler. Placing the process tubes individually in the thermal cycler is inefficient, time consuming, and can be difficult to automate. Further, such processes are susceptible to human error.

In some instances, racks containing the process tubes can be placed directly in the thermal cycler. However, this approach too has drawbacks because the process tubes may shift in the rack during handling and transport and consequently will likely not line up correctly with the heaters of the thermal cycler. Additional intervention by a lab technician is required align the tubes and fit them into the heaters of the thermal cycler. Furthermore, if the process tubes are not securely connected to the rack, the process may become dislodged during marking of the process tubes, being pulled up and out of the rack by the stamping apparatus.

Much of the difficulty with the handling and transport of process tubes in a rack stems from the shape of the tubes generally used in amplification processes. Process tubes are often conical in shape, having an outside diameter larger at the top of the process tube than at the bottom of the process tube. Some process tubes are cylindrical in shape, having a constant diameter from top to bottom. The ports of the rack in which the process tubes are placed must be of a greater diameter than the largest outside diameter of the process tubes (at the top of the process tube). To address the tolerances associated with manufacturing the process tubes and the rack, the ports in the rack are often appreciably larger than the outside diameter of the process tubes, allowing the tubes to move around in the rack and potentially fall out. Without a secure fit in the rack, the process tube may tilt to one side or another. With multiple process tubes in a rack, the tilting process tubes may bump into each other and break and/or cause loss of sample and/or reagents stored therein. Furthermore, it can be very difficult to line up the differently tilted process tubes into the rigid heaters of the thermal cycler.

Thus, there is a need for process tubes and a tray that fit securely together to allow for safe and efficient handling and transport of the process tubes prior to and during amplification. Furthermore, there is a need for process tubes that still have an ability to adjust or float within the tray in order to facilitate alignment with the heaters of a thermal cycler.

The discussion of the background herein is included to explain the context of the inventions described herein. This is not to be taken as an admission that any of the material referred to was published, known, or part of the common general knowledge as at the priority date of any of the claims.

SUMMARY

Certain embodiments disclosed herein contemplate a process tube having a securement region that includes an annular ledge, a protrusion, and a neck between the ledge and the protrusion. The process tube also includes a body extending below the protrusion and a top ring extending vertically up from the annular ledge which defines an opening to the tube.

In certain embodiments, an outside surface of the neck can be parallel to a longitudinal axis through the process tube. The protrusion can include an apex, an upper slope from the apex to the neck, and a lower slope from the apex to the body. The angle of the upper slope on the protrusion can be steeper than the angle of the lower slope on the protrusion. The annular ledge of the process tube can have an upper surface, a lower surface, and an outside surface. The protrusion can have a larger outside diameter than the outside diameter of the neck. The annular ledge can have a larger outside diameter than the outside diameter of the protrusion. The process tube can further include a base below the body which defines a bottom of the process tube.

Certain embodiments disclosed herein include a process tube strip having a plurality of process tubes. The plurality of process tubes is connected by a tab adjoining the annular ledges of the plurality of tubes.

Certain embodiments contemplate a process tube having an annular ledge extending laterally from the tube, the annular ledge comprising an upper surface, a lower surface, and an outer surface. The process tube can include a top ring extending vertically up from the upper surface of the annular ledge which defines an opening to the process tube. The process tube can further include an annular protrusion extending laterally from the process tube, at a location on the tube below the annular ledge. The protrusion can have an apex, an upper slope, and a lower slope. The process tube can include a neck between the annular ledge and the protrusion, a body below the protrusion, and a base which defines a bottom of the tube.

Embodiments of the process tube disclosed can be configured to securely fit in a carrier tray. The carrier tray can have a shelf and a base, such that the shelf has a plurality of ports through a top of the shelf, and the ports having an interior wall. In certain embodiments, the protrusion of the process tube disclosed can have a larger outside diameter than the diameter of the port in the carrier tray. The neck of the process tube can have a smaller outside diameter than the diameter of the port in the carrier tray. The process tube can be securely fit into a port of the carrier tray.

In certain embodiments of the process tube, the lower surface of the annular ledge of the process tube can rest on an exterior of the shelf top and the upper slope of the protrusion can rest on a bottom edge of the interior wall of the port. A gap can exist between the neck of the process tube and the interior wall of the port and the gap can allow the process tube to tilt or adjust within the port of the carrier tray.

Further embodiments of the disclosure contemplate a system having a carrier tray with a plurality of ports therethrough and a process tube having a securement region. The securement region of the process tube can include an annular ledge, a neck, and a protrusion. The securement region of the process tube can fit securely in a port of the carrier tray. In this system, the annular ledge and protrusion of the process tube can have outside diameters that are larger than the diameter of the port of the carrier tray and the neck of the process tube can have an outside diameter that is smaller than the diameter of the port. When the process tube is securely fit in the port of the carrier tray, the process tube can tilt or adjust within the port of the carrier tray.

DETAILED DESCRIPTION

Before the embodiments are further described, it is to be understood that this invention is not limited to particular embodiments described, as such may, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range is encompassed within the embodiments. The upper and lower limits of these smaller ranges may independently be included in the smaller ranges and are also encompassed within the embodiments, subject to any specifically excluded limit in the stated range. Where the stated range includes one or both of the limits, ranges excluding either both of those included limits are also included in the embodiments.

Unless defined otherwise, all technical and scientific terms used herein have the same meaning as commonly understood by one of ordinary skill in the art to which the embodiments belong. Although any methods and materials similar or equivalent to those described herein may also be used in the practice or testing of the embodiments, the preferred methods and materials are now described.

It must be noted that as used herein and in the appended claims, the singular forms "a," "and," and "the" include plural referents unless the context clearly dictates otherwise. Thus, for example, reference to "a method" includes a plurality of such methods and equivalents thereof known to those skilled in the art, and so forth.

Throughout the description and claims of the specification the word "comprise" and variations thereof, such as "comprising" and "comprises," is not intended to exclude other additives, components, integers or steps.

The process tubes and carrier tray described herein can be used together to provide a safe and efficient system of preparing, storing, and transporting the process tubes prior to use in a thermal cycler and also for positioning the process tubes accurately and securely in the thermal cycler during amplification.

Figure 1A:
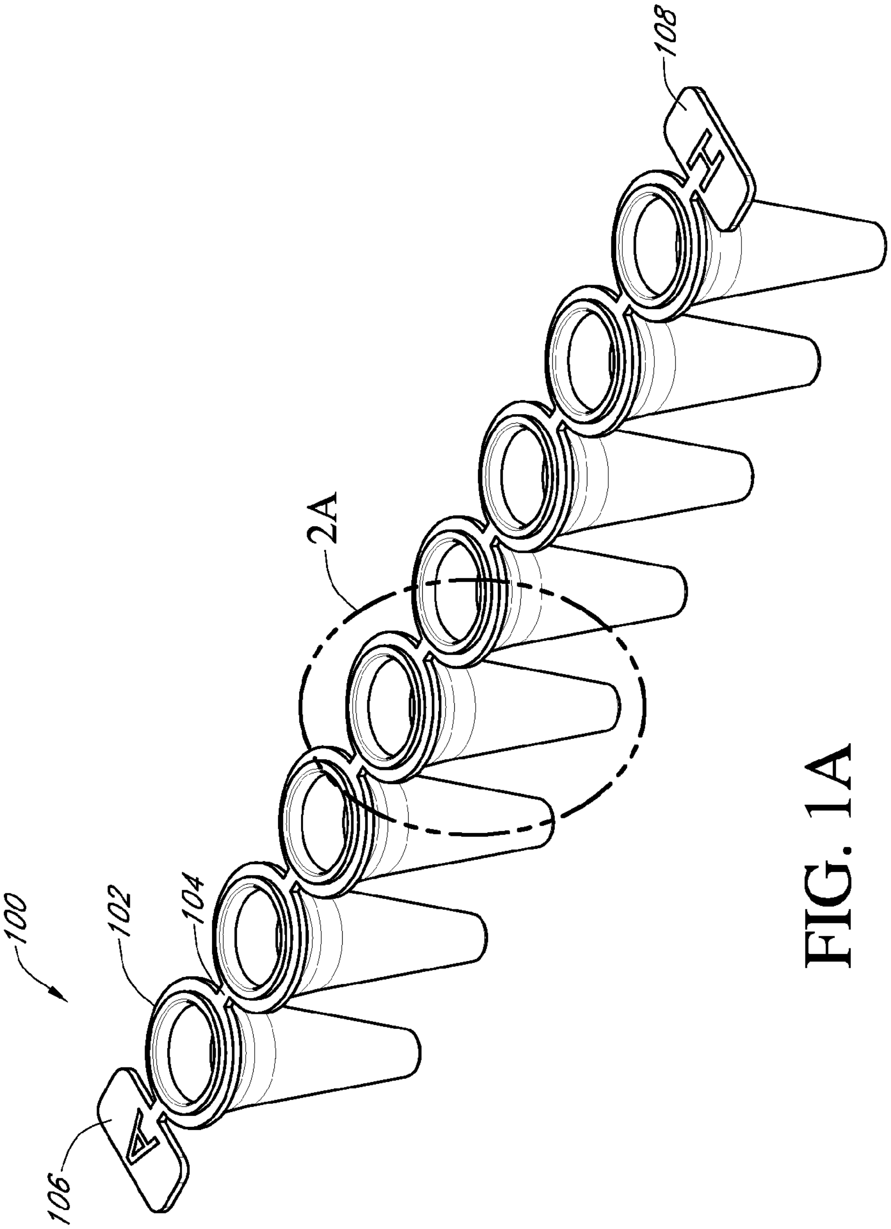
FIG. 1A shows an isometric view of an exemplary process tube strip as described herein.
Figure 1B:
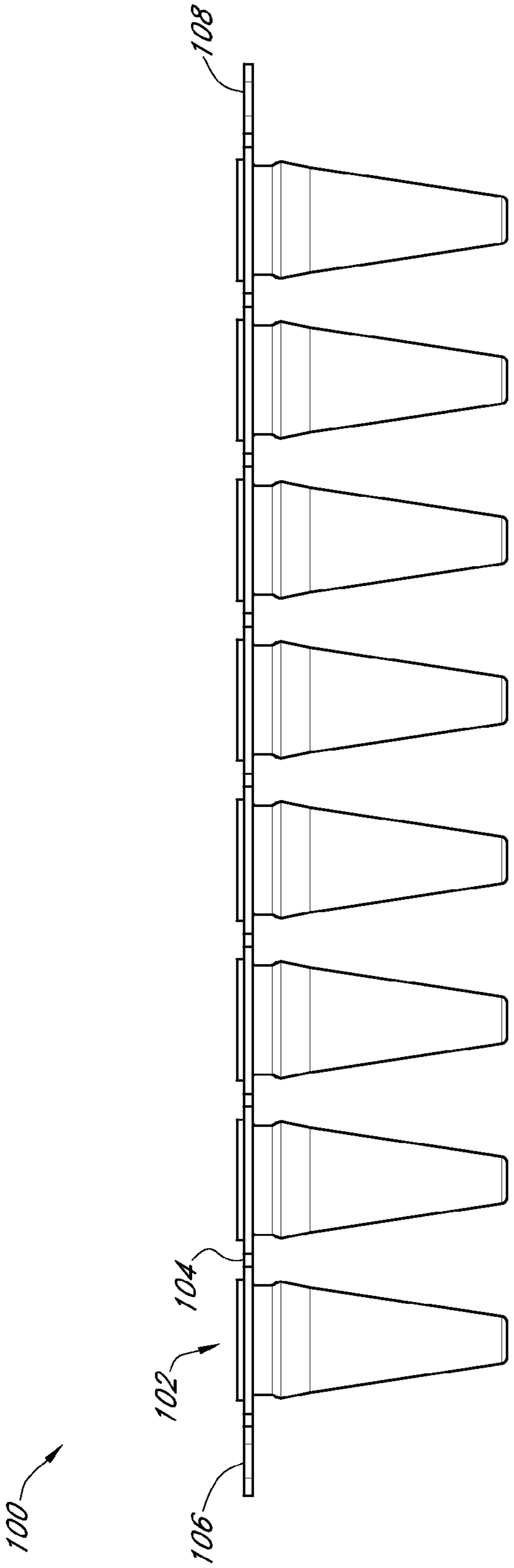
FIG. 1B is a side plan view of the process tube strip of FIG. 1A.
Figure 1C:
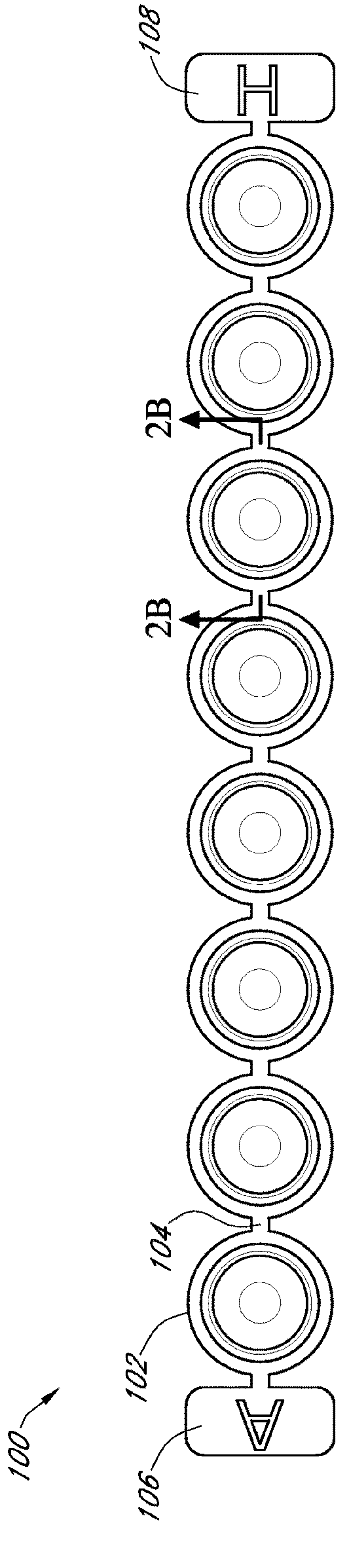
FIG. 1C is a top view of the process tube strip of FIG. 1A.

FIG. 1A shows an isometric view of an exemplary process tube strip 100 according to the embodiments described herein. FIG. 1B is a side plan view of the process tube strip of FIG. 1A. FIG. 1C is a top view of the process tube strip of FIG. 1A. As shown in FIGS. 1A-1C, the process tube strip 100 is a collection of process tubes 102, connected together by a connector tab 104. The exemplary process tube strip 100 can also include a top end tab 106, as shown in FIGS. 1A-1C, indicating the top of the process tube strip 100 and a bottom end tab 108 indicating the bottom of the process tube strip 100. The process tube strip 100 shown in FIGS. 1A-1C includes eight process tubes 102 connected together in the process tube strip 100. One skilled in the art will immediately appreciate however, that in other embodiments, the process tube strip 100 can include, for example any other number of process tubes, e.g., 40, 30, 20, 19, 18, 17, 16, 15, 14, 13, 12, 11, 10, 9, 7, 6, 5, 4, 3, or 2 process tubes 102 connected in the process tube strip 100. An embodiment of the process tube strip 100 can include an insignia or indication on the upper surface of the top and bottom end tabs 106, 108. In one embodiment, the top end tab 106 can be marked with an "A" indicating the top of the process tube strip 100 and the bottom end tab 108 can be marked with the letter of the alphabet corresponding to the number of process tubes 102 in the process tube strip 100 (for example, an "H" would be marked on the bottom end tab 108 of the process tube strip 100 for a process tube strip 100 having eight process tubes 102 connected together in the process tube strip 100). The skilled artisan will readily appreciate, however, that various other characters, e.g., alphanumeric characters, such as "1" and "8" can also be readily used in marking the top and bottom end tabs of process tube strip 100, to achieve the same purpose. Thus, the top and bottom end tabs 106, 108 can be used to indicate the top and bottom of a process tube 102 and the number of process tubes 102 in a process tube strip 100. In addition, the end tabs 106, 108 can be marked with a color marking, a barcode, or some other designation to identify, for example, the contents of the process tubes 102, the assay type being performed in the process tube strip 100, and the date and location of manufacture of the process tube strip 100.

Figure 1D:
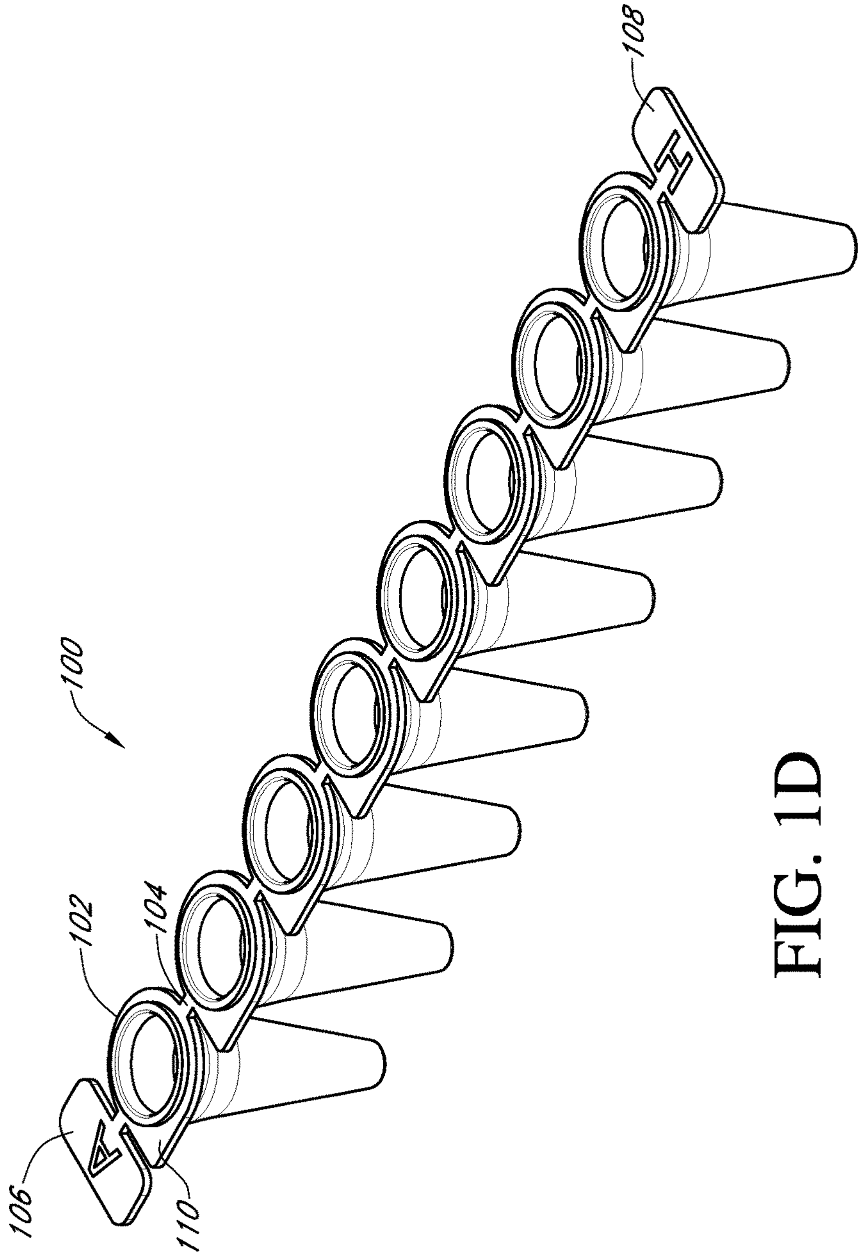
FIG. 1D shows an isometric view of another exemplary process tube strip as described herein.
Figure 1E:
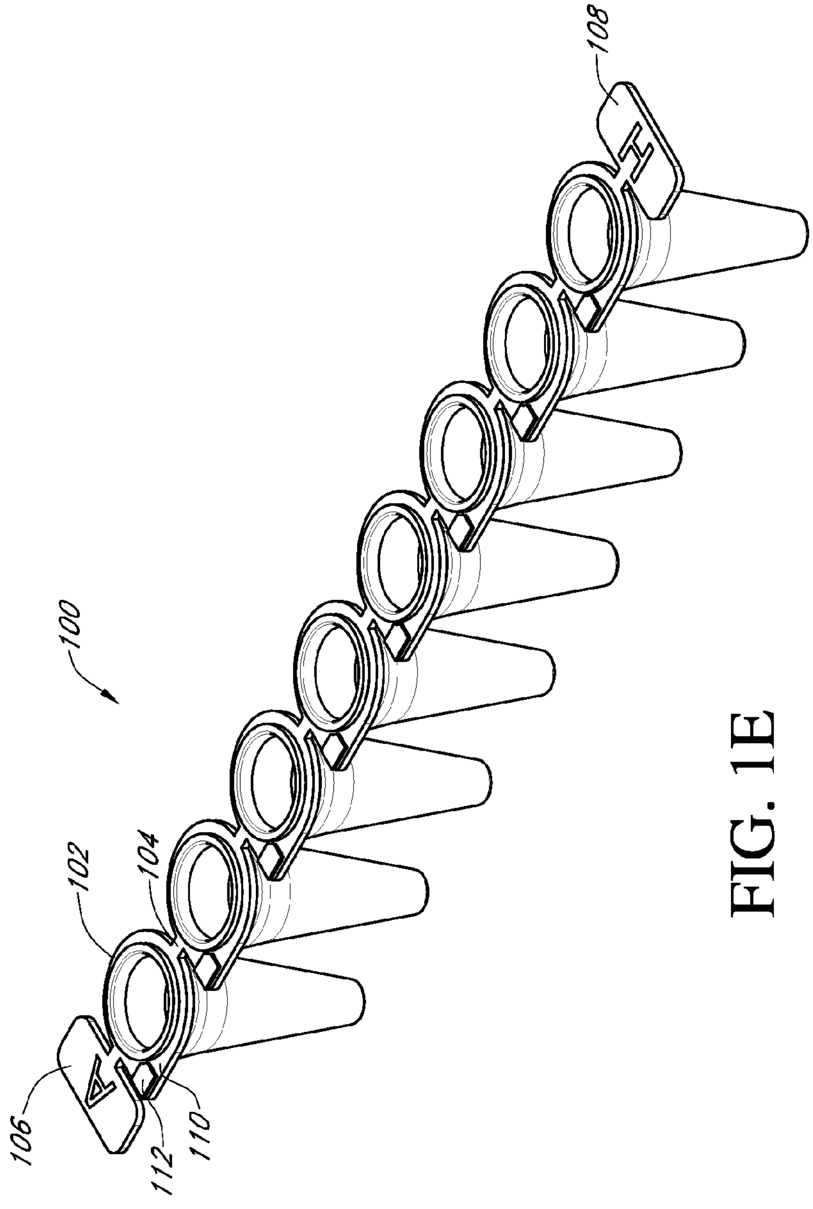
FIG. 1E shows an isometric view of another exemplary process tube strip as described herein.

FIG. 1D is another embodiment of the process tube strip 100 that includes a ledge extension 110 on each of the process tubes 102. FIG. 1E is an additional embodiment of the process tube strip 100 that includes a tube tag 112 positioned on the ledge extension 110 of each process tube 102. These embodiments will be discussed in further detail below.

Process tubes 102 can be receptacles for, or house, solids or liquids. For example, process tubes 102 can hold reagents and/or samples, e.g., nucleic acid samples to be used in amplification assays. The process tubes 102 can be circular in cross-section, but other cross sections are possible and consistent herewith. The process tubes 102 can be manufactured via a unitary construction, although in certain instances the process tubes may be constructed from two or more parts fused or otherwise joined together as applicable. Typically, the process tubes 102 have an opening that is configured to accept/receive a pipette tip for deposit and/or retrieval of fluids within the process tube 102.

In some embodiments, the process tubes 102 can be constructed from polypropylene or other thermoplastic polymers known to those skilled in the art. Alternatively, process tubes 102 can be constructed from other appropriate materials, such as polycarbonate or the like. In some embodiments, the polypropylene is advantageously supplemented with a pigment, such as titanium dioxide, zinc oxide, zirconium oxide, or calcium carbonate, or the like. Preferably, the process tubes 102 are manufactured using materials such that they do not fluoresce and thus do not interfere with detection of the amplified nucleic acid in the process tubes 102.

Figure 2A:
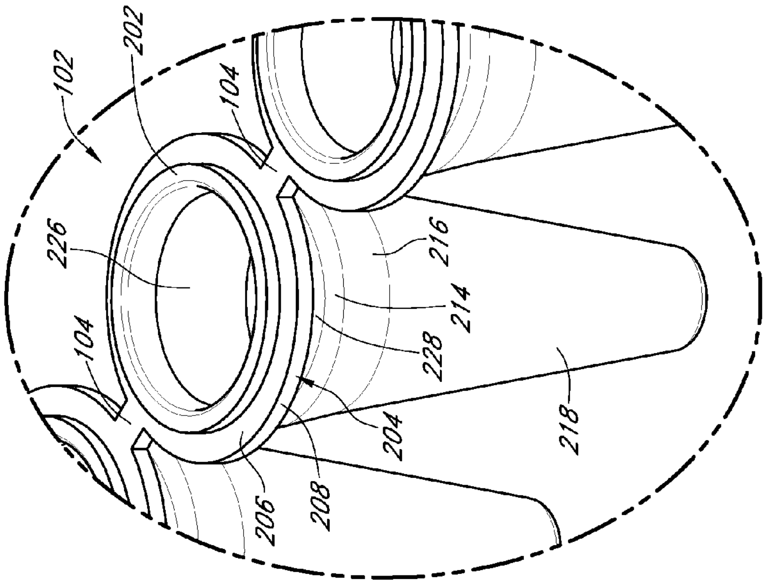
FIG. 2A is an isometric view of an exemplary, single process tube as described herein.
Figure 2B:
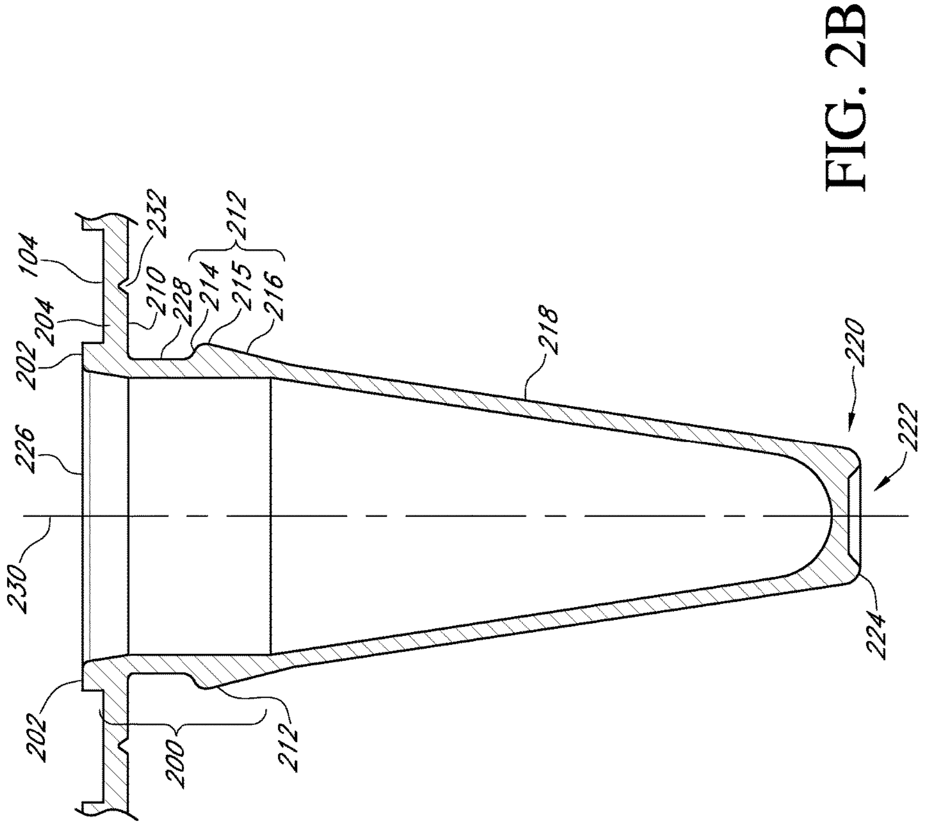
FIG. 2B is a cross-sectional view of the process tube of FIG. 2A taken along line 2B in FIG. 1C.

FIGS. 2A and 2B show, respectively, an isometric and a cross-sectional view of an exemplary single process tube 102. Connector tabs 104 are shown in FIG. 2A, connecting the process tube 102 to other process tubes 102 on either side of the process tube 102. In FIG. 2B, the shown connector tab 104 includes a connector recess 232 on the underside of the connector tab. In some embodiments, the connector recess 232 provides a separation point to easily break apart different process tubes 102 connected as part of a process strip 100. The process tubes 102 can be broken apart by the end user in order to mix and match different process tubes 102 having different dried reagents, and rearranging the process tubes in the carrier tray 300 to match the necessary operation of the amplification assay in the thermal cycler. A connector tab 104 can also be positioned between the process tube 102 at the end of a process tube strip 100 and the top or bottom end tab 106, 108. Such a connector tab 104 allows the end process tube 102 to be removed easily and also mixed and matched with process tubes 102 from other process tube strips 100 or to be used individually in a thermal cycler.

As shown in FIGS. 2A and 2B, the process tube 102 can have a top ring 202, the top ring 202 defining an opening 226 at the top of the process tube 102. The top ring 202 extends around the circumference of the opening 226. As part of the process tube 102, an annular ledge 204 extends laterally out from the side of the process tube 102 below the top ring 202. In this manner, the top ring 202 extends upwards from an upper surface 206 of the annular ledge 204. In addition to the upper surface 206, the annular ledge 204 is also defined by an outer surface 208 and a lower surface 210. Below the annular ledge 204 is a neck 228 of the process tube 102, which extends vertically from the annular ledge 204, parallel to the longitudinal axis 230 of the process tube 102. As shown in FIG. 2B, the exterior of the process tube 102 at the neck 228 can be parallel to a longitudinal axis 230 running vertically through the process tube 102. In another embodiment, the exterior neck 228 can be at an angle to the longitudinal axis 230 to aid in removal of the process tube 102 from an injection mold during the manufacturing process.

Below the neck 228 of the exemplary process tube 102 shown in FIGS. 2A-2B, is a protrusion 212 extending laterally from the side of the process tube 102. The protrusion 212 is defined by an upper slope 214 when extends from the neck 228 to an apex 215 of the protrusion 212. The apex 215 of the protrusion 212 has the largest outside diameter of the protrusion 212 and then the protrusion 212 includes a lower slope 216 which extends from the apex 215 down the exterior of the process tube 102. The upper slope 214 of the protrusion 212 slopes away from the longitudinal axis 230 and the lower slope 216 slopes back towards the longitudinal axis 230. In some embodiments, as shown in FIGS. 2A-2B, the angle of the upper slope 214 on the protrusion is steeper than the angle of the lower slope 216 on the protrusion 212. The lower slope 216 of the protrusion 212 meets a longer body portion 218 of the process tube 102. The body 218, like the lower slope 216 of the protrusion 212, slopes towards the longitudinal axis 230, but has a less steep angle than the lower slope 215 of the protrusion 212. The body 218 extends to a base 220 of the process tube 102. The base 220 includes an annular bottom ring 224 on the bottom of the process tube 102, defined by a divot 222 in the bottom of the process tube 102. In this embodiment, the top ring 202, the annular ledge 204, the neck 228, the protrusion 212, and the body 218 are coaxial with the longitudinal axis 230.

The annular ledge 204, neck 228, and protrusion 212 together define a securement region 200 of the process tube 102. As will be explained in detail below, the securement region 200 provides a way to easily and securely attach the process tube 102 (or plurality of process tubes 102 in the form of a process strip 100) to a carrier tray for transport and later processing in the heater of an thermal cycler.

Figure 3A:
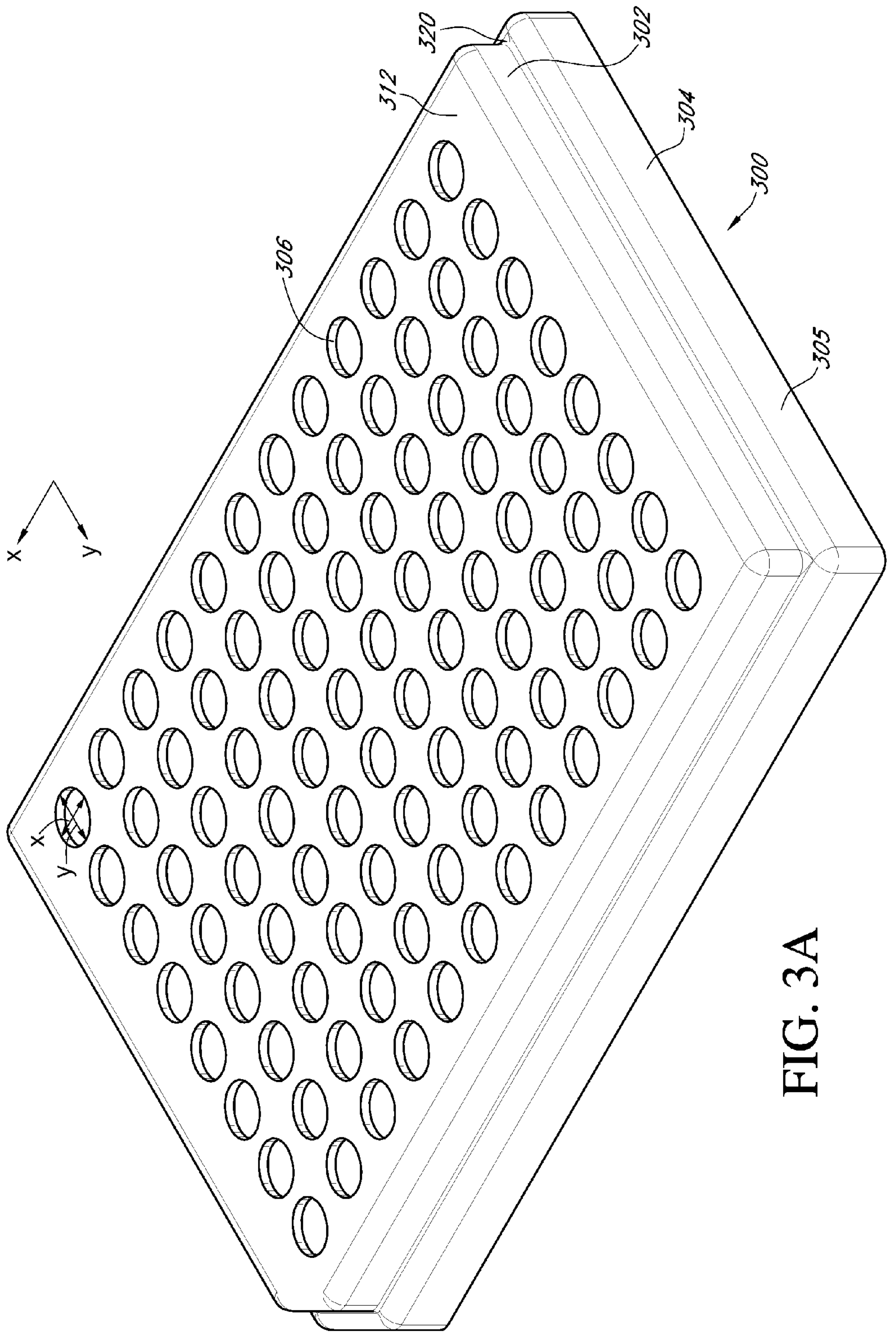
FIG. 3A shows an exemplary carrier tray, as described herein.

As described above, the process tubes 102 can be manufactured as a strip 100 of tubes 102 connected together by a connector tab 104. Multiple process tube strips 100 can then be inserted securely in a carrier tray 300. FIG. 3A shows an exemplary carrier tray 300. As seen in FIG. 3A, the carrier tray 300 can house a plurality of ports 306 in a shelf 302 of the carrier tray 300. The plurality of ports 306 can be configured to receive the individual process tubes 102, and the number of ports 306 in a column of the carrier tray 300 can be advantageously designed to fit the length of the process tube strips 100. Thus, the number of ports 306 in the y-direction can be designed to correspond to the number of process tubes 102 in a process tube strip 100. In one embodiment, the carrier tray 300 can have eight ports 306 in the y-direction such that a process tube strip 100 consisting of eight process tubes 102 can be inserted and secured in the ports 306 of the carrier tray 300 in the y-direction.

In one embodiment, the ports 306 in the carrier tray 300 are elliptical in shape, having a larger cross-sectional diameter in the y-direction. In this manner, the larger diameter cross-sections of the elliptical ports 306 are lined up in the same direction as the process tube strips 100 when inserted in the carrier tray 300.

Figure 3B:
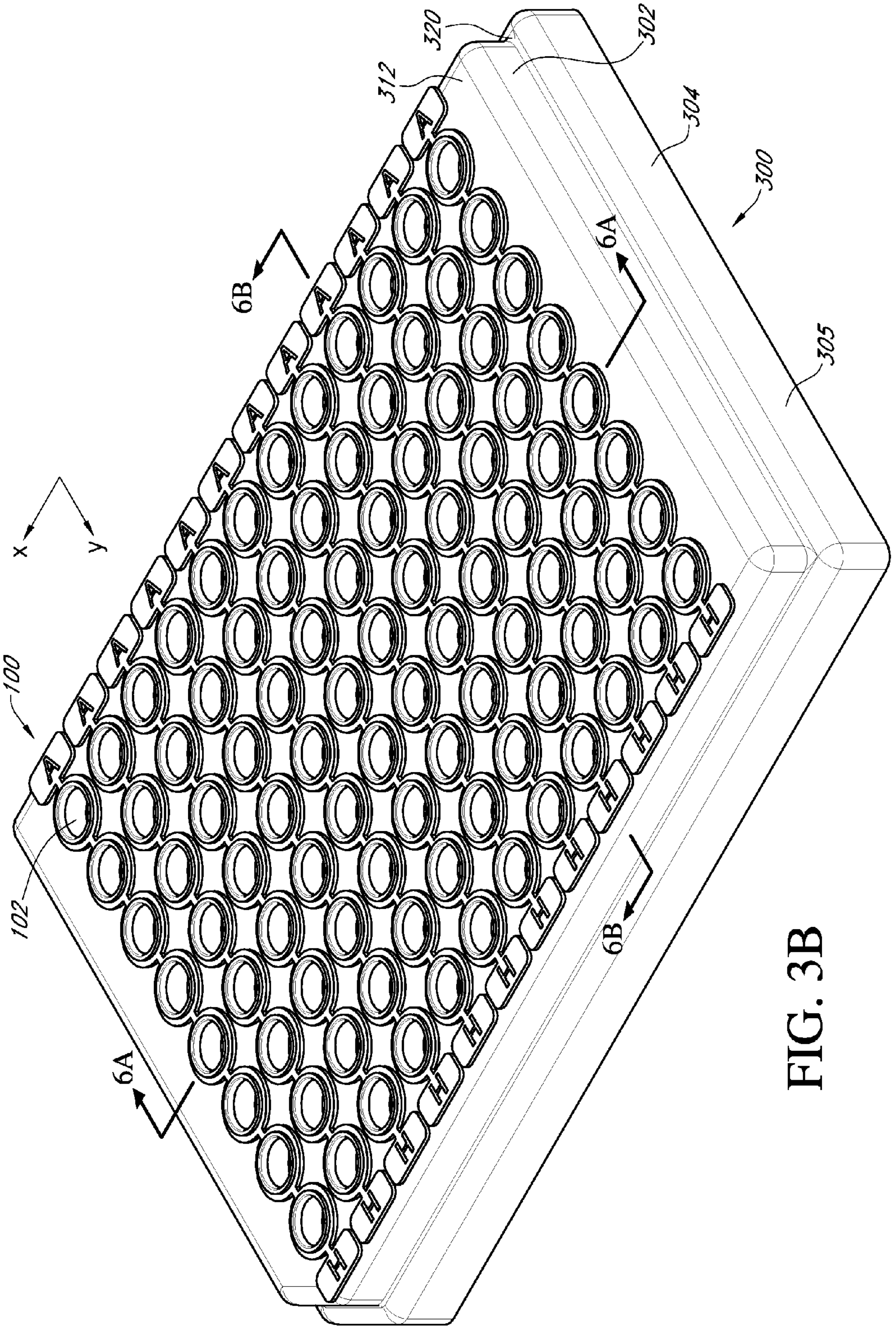
FIG. 3B shows a plurality of exemplary process tube strips in the carrier tray of FIG. 3A.

FIG. 3B shows a plurality of process tube strips 100 securely fit in an exemplary carrier tray 300. Once the process tubes 102 are inserted securely in the carrier tray 300, assay reagents, e.g., amplification and detection reagents, can be added to the process tubes 102 in an automated manner. In some embodiments, liquid reagents can be pipetted into the individual process tubes 102 and then the carrier tray 300 can optionally be placed in a drier to dry the liquid reagents in the bottom of the process tubes as a solid mass formed to the shape of the internal base 220 of the process tube 102. In some embodiments, liquid reagents are not dried down in the process tubes 102. In some embodiments, each process tube 102 in a carrier tray 300 can be deposited with identical reagents. In other embodiments, some or each of the process tubes 102 in process tube strip 100 can be filled with differing reagents or samples.

Once filled with the desired reagents, e.g., following drying of the reagents in embodiments wherein the reagents are dried, or simply following deposition of the reagents in embodiments wherein the reagents are not dried, the process tubes 102 can be marked with an indicator to identify the contents (for example, the specific reagents) of the process tubes 102. In some embodiments, marking of the process tubes 102 can be accomplished by hot stamping the top ring 202 of the process tubes 102 with a specific color indicating the contents (e.g., reagents) of the process tubes 102. The top ring 202 also provides a surface to which an adhesive seal can be applied to seal the opening 226 of the process tube 102.

As described above, FIG. 1D shows a process tube strip 100 wherein each process tube 100 includes a ledge extension 110 extending from one side of the annular ledge 204 of the process tube 100. The ledge extension 110 provides additional surface area on the annular ledge 204 for marking of the individual process tubes 102. In one embodiment, the ledge extension 110 can be pre-marked with an alphanumeric identifier (e.g., A, B, C, etc, or 1, 2, 3, etc.) to identify an individual process tube 102 within a process tube strip 100. In one embodiment, as an alternative to hot stamping the top ring 202, the ledge extension 110 of the process tubes 102 can be hot stamped, or otherwise marked, to identify the contents (e.g., reagents) of the process tubes 102 following the deposit of the reagents in the process tubes 102. Furthermore, a 2-D bar code (ink or laser) can be printed directly on the ledge extension 110.

As shown in FIG. 1E, the individual process tubes 102 of the process tube strip 100 can include a tube tag 112 affixed to the top of the ledge extension 110. The tag 112 can be used in addition to, or in conjunction with, marking (e.g., hot stamping) the top ring 202 of the process tubes 102 to identify the contents, such as reagents, in a particular process tube 102. The tag 112 can be a 2-dimensional matrix bar code (for example, a QR code or Aztec code) encoded with data identifying the contents of the associated process tube 102. In using a tag 112 to indicate the contents of the process tube 102, a camera (e.g., a CCD camera) can be used to scan and verify the contents of the process tube 102 and ensure the correct amplification assays are being performed with the associated reagents. The camera can efficiently and quickly verify the contents of each process tube 102 by reading the tag 112, thus avoiding the possibility of user error in pairing incorrect reagents with a specific amplification assay required for a given polynucleotide sample.

In some instances, identical reagents can be added to each process tube in a carrier tray 300. In one example, each tube strip 100 can include eight process tubes 102 and then 12 tube strips can be securely fit into a 96-port carrier tray 300. Identical reagents can then be added to each of the 96 process tubes in the carrier tray 300. If all process tubes 102 are provided with identical reagents, all process tubes 102 in the entire carrier tray 300 can be hot stamped with the same color. A number of carrier trays 300 can be stacked and sent together to the end user. In some embodiments, each or some of the process tubes 102 in tube strip 100 can include different reagents. In such instances, process tubes 102 that contain identical reagents can be marked with the same color. Different colors can be used to identify process tubes 102 containing different reagents.

The end user may need different stamped process tubes 102 to run different amplification assays with the different reagents provided. In some instances the end user may need to use different reagents in an amplification assay, so a carrier tray 300 having process tubes 102 of all the same reagents could not be used. In this case, the end user can remove one or more process tube strips 100 from a single-color carrier tray 300 and exchange them with differently colored process tube strips 100 in a different carrier tray 300 to achieve the desired number and type of reagents for a given amplification assay. It is also contemplated that the manufacturer could provide the end user with a carrier tray 300 having different colored process tube strips 100.

The end user can further refine the collection of different reagents in an amplification assay by breaking apart an individual process tube strip 100 at the connector recess 232 between process tubes 102. For example, an eight-tube process tube strip 100 can be broken into smaller collections of process tubes 102 having 1, 2, 3, 4, 5, 6, or 7 process tubes 102. Breaking apart the process tube strips 100 allows the end user to include process tubes 102 of different reagents in the same column of the carrier tray 300.

Figure 4:
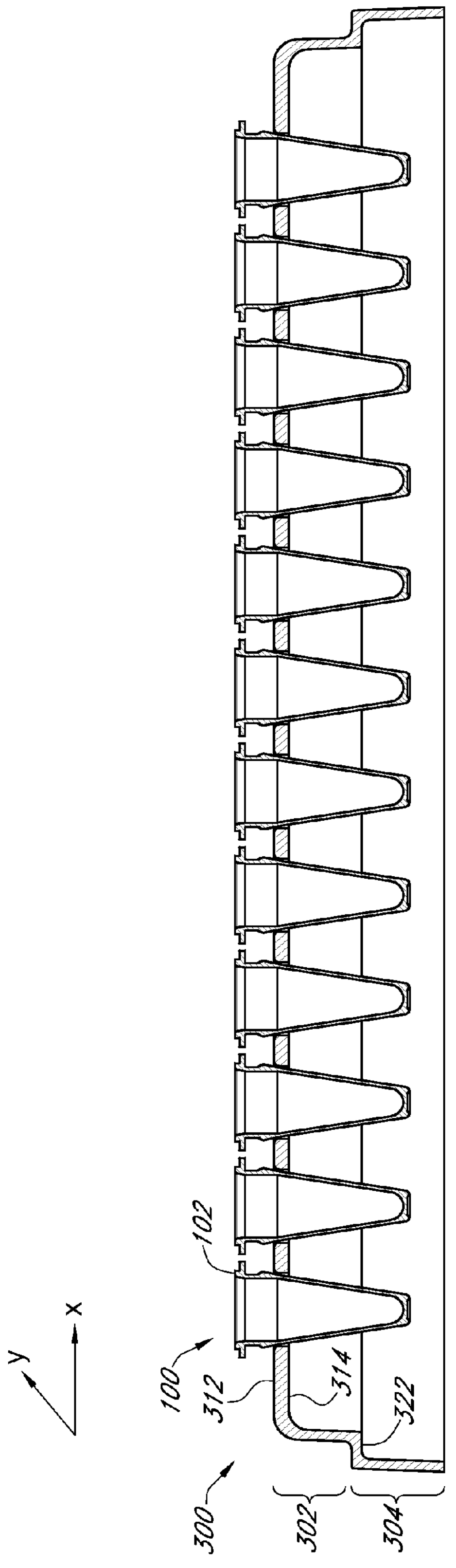
FIG. 4 is a cross-sectional view of 12 process tubes positioned in the carrier tray prior to securing the process tubes in the carrier tray.

As described above, FIG. 3B provides an illustration of the process tubes 102 when the process tubes are already securely fit into the carrier tray 300. FIG. 4 is a cross-sectional view of 12 process tubes 102 positioned in the carrier tray 300 prior to securing the process tubes 102 in the carrier tray 300. This view is analogous to the cross-sectional view 6A shown in FIG. 3, but shows the process tubes 102 resting in the ports 306 of the carrier tray 300 prior to securing the process tubes 102 in the carrier tray 300. As shown in FIG. 3B and FIG. 4, the carrier tray 300 has a base 304 and a shelf 302, the base 304 being wider and longer than the shelf 302 and, thus, having a larger planar surface area than shelf 302. The shelf 302 of the carrier tray 300 includes a shelf side 308 and a shelf top 310. The shelf top 310 is the horizontal, planar portion of the shelf 302 and covers the top of the carrier tray 300. The shelf top 310 includes an exterior surface 312 and an interior surface 314. As the base 304 of the carrier tray 300 is wider and longer than the shelf 302, the base 304 includes a bridge 320 running horizontally connecting the shelf side 308 and a base side 305. The bridge 320 includes an interior side 322. The shelf side 308 of the shelf 302 on the carrier tray 300 extends down from the shelf top 310 and joins the base 304 of the carrier tray 300 at the bridge 320. As shown in FIG. 4, the process tubes 102 of a process tube strip 100 can be positioned in the ports 306 in the shelf 302 of the carrier tray 300.

Figure 5:
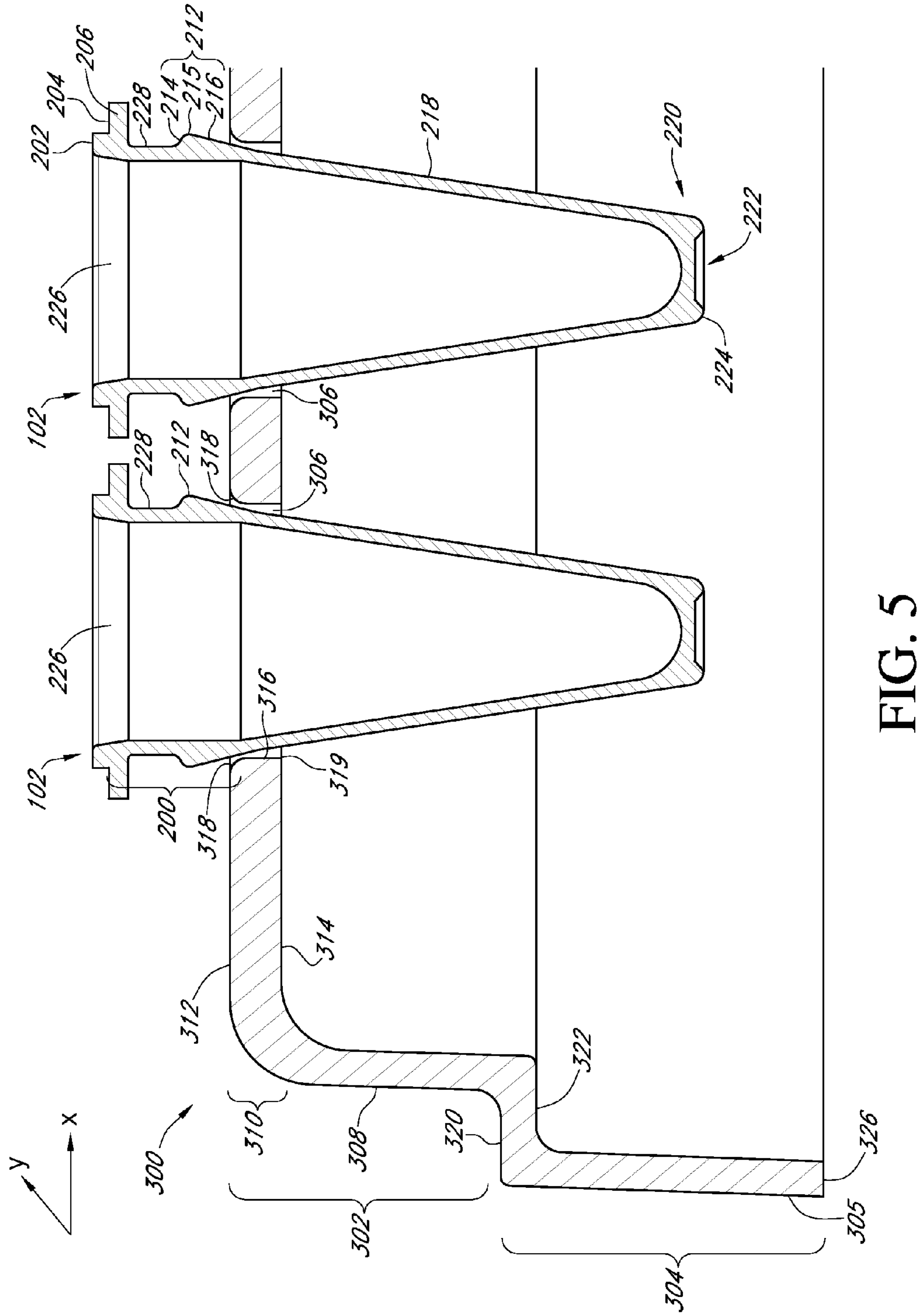
FIG. 5 is a cross-sectional view of two exemplary process tubes positioned in the carrier tray prior to securing the process tubes in the carrier tray.

FIG. 5 is a close-up, cross-sectional view of two exemplary process tubes 102 positioned in an exemplary carrier tray 300, prior to securing the process tubes 102 in the carrier tray 300. Prior to securing a process tube 102 in the carrier tray 300, the process tube 102 is able to rest in the port 306 of the carrier tray 300. The outside diameter of the body 218 of the process tube 102 is smaller than the diameter of the port 306, thus, the body 218 of the process tube 102 can be inserted through the port 306. The protrusion 212 on the process tube 102 has a larger diameter than at least one diameter of the port 306. For example, in the instance of the port 306 being elliptical, the smaller diameter of the port 306 (for example the width diameter in the x-direction of FIGS. 3A and 3B) is smaller than the diameter of the protrusion 212. In some embodiments, the larger diameter of the port 306 (for example the length diameter in the y-direction of FIGS. 3A and 3B) can be larger than the diameter of the protrusion 212. Thus, when the body 218 of the process tube 102 is inserted into the port 306, the body 218 enters the underside area of the carrier tray 300, but a top portion of the process tube 102, including the securement region 200 (comprising the protrusion 212, the neck 228, and the annular ledge 204) and the top ring 202, is prevented from entering the port 306. In this manner, the protrusion 212 comes to rest on a top edge 318 of the port 306. More specifically, the lower slope 216 of the protrusion 212 comes to rest on the port top edge 318.

In some embodiments, the apex 212 of the protrusion 212 is circular, having a constant outside diameter. For an elliptical port 306, in one embodiment, the port 306 can have a length diameter larger than the width diameter. In this embodiment, the diameter of the port 306 width (in the x direction) can be less than the diameter of the apex 215 of the protrusion 212. Thus, the process tube 102 comes to rest, at the protrusion 212, on the top edge 318 of the port 306. In one embodiment, the length diameter (in the y direction) of the port 306 can be greater than the diameter of the apex 215 of the protrusion 212. Thus, a small gap on two ends (in the y-direction) of the port 306 is provided that facilitates easier securement of the process tube 102 in the port 306 and also facilitates easier removal of the process tube 102 from the port 306, if needed. In other embodiments, the port 306 can be round, having a constant diameter.

As the process tube 102 rests in the port 306 against the port top edge 318, a force can be applied to the top of the process tube 102 to press the process tube 102 further into the port 306 to secure the process tube 102 in the port 306 of the carrier tray 300. The force to secure the process tube 102 into the port 306 can be applied to the top ring 202 of the process tube 102 or the force can be applied to the upper surface 206 of the annular ledge 204.

Securing the process tube 102 in the port 306 initially involves applying sufficient force to the top of the process tube 102 to force the lower slope 216 of the protrusion 212 into the port 306. The lower slope 216 is angled towards the longitudinal axis 230 of the process tube 102. As continued pressure is applied to the top of the process tube 102, the lower slope 216 of the protrusion 212 slides down along the port top edge 318 until the apex 215 of the protrusion 212 reaches the port top edge 318. The port top edge 318 can be rounded or sloped to facilitate the travel of the protrusion 212 through the port 306.

As the process tube 102 is pushed into the port 306, the portions of the lower slope 216 of the protrusion 212 that have passed into the port 306 do not contact the port interior wall 316 because the lower slope 216 is angled towards the longitudinal axis 230. The lower slope 216 of the protrusion 212 gradually widens (the outside diameter increases) as the lower slope 216 extends upwards towards the apex 215 of the protrusion 212. The wider the diameter of the lower slope 216, the greater resistance to pushing the process tube 102 into the port 306. Thus, a resistive force is generated which counters the force applied to push the process tube 102 into the port 306. The resistive force against the process tube 102 increases (and the force necessary to push the process tube 102 increases), the farther down the process tube 212 travels into the port 306. The resistive force against the process tube 102 continues to increase until the apex 215 of the protrusion 212 reaches the port top edge 318.

In an embodiment of the carrier tray 300 having elliptical ports 306, the larger diameter of the port 306 in the y direction may more easily allow the process tube 102 to be pushed into the port 306 and secured in the carrier tray 300, thus reducing the force required to secure the process tube. An elliptical port 306 can provide extra space (e.g., a gap) between the protrusion 212 of the process tube 102 and the port interior 316 on two ends that allows the process tube 102 to flex and elongate in the y direction and compress in the x direction.

Once the entirety of the lower slope 216 passes through the port top edge 318, and the apex 215 of the protrusion passes through the port top edge 318, the apex 215 of the protrusion 212 comes into contact with the port interior wall 316. The apex 215 is the widest portion (largest outside diameter) of the protrusion 212. As the apex 215 is being fit through the port 306 and pressed against the port interior wall 316, the process tube 102 undergoes maximum strain and is maximally flexed. As continued force is applied to the top of the process tube 102, the apex 215 is forced to slide down the port interior wall 316 until it completely passes through the port 306 at the bottom edge 319 of the port 306. Once the apex 215 breaches the bottom edge 319, the strain on the process tube 102 is released and the process tube 102 "snaps" securely into place in the port 306 and becomes secured in the carrier tray 300. The force necessary to secure each process tube 102 of the process tube strips 100 in a carrier tray 300 can range from approximately 0.7 lbs. force to approximately 1.7 lbs. force. In one embodiment, the force necessary to insert and secure process tube 102 in a port 306 can be approximately 1 lb. force. In one embodiment, the force necessary to secure a process tube 102 in a port 306 can be approximately 1.18 lbs. force.

The carrier tray 300 can be advantageously designed for efficient stacking and transport of the carrier trays 300. The carrier tray 300 can be constructed from polycarbonate resin thermoplastic. Referring to FIGS. 3, 4, and 5, the carrier tray 300 can include a bridge 320 at the top of the base 220. The bridge 320 provides a platform on which the bottom surface 326 of another empty carrier tray 300 can positioned. When two carrier trays 300 are stacked on top of each other, the bridge interior 322 of a top carrier tray 300 comes to rest on the shelf top 310 of a bottom carrier tray 300 and the bottom surface 326 of the top carrier tray 300 comes to rest on the bridge 320 of the bottom carrier tray 300.

When the carrier trays 300 are populated with the process tube strips 100, they can be efficiently stacked in a similar manner. The body 218 of the process tubes 102 in a top carrier tray 300 can be placed in the opening 226 of the process tubes 102 in a bottom carrier tray 300. Likewise, the process tubes 102 in the top carrier tray 300 can further receive the body 218 of the process tubes 102 in another carrier tray 300 to be stacked on top of it.

Figure 6A:
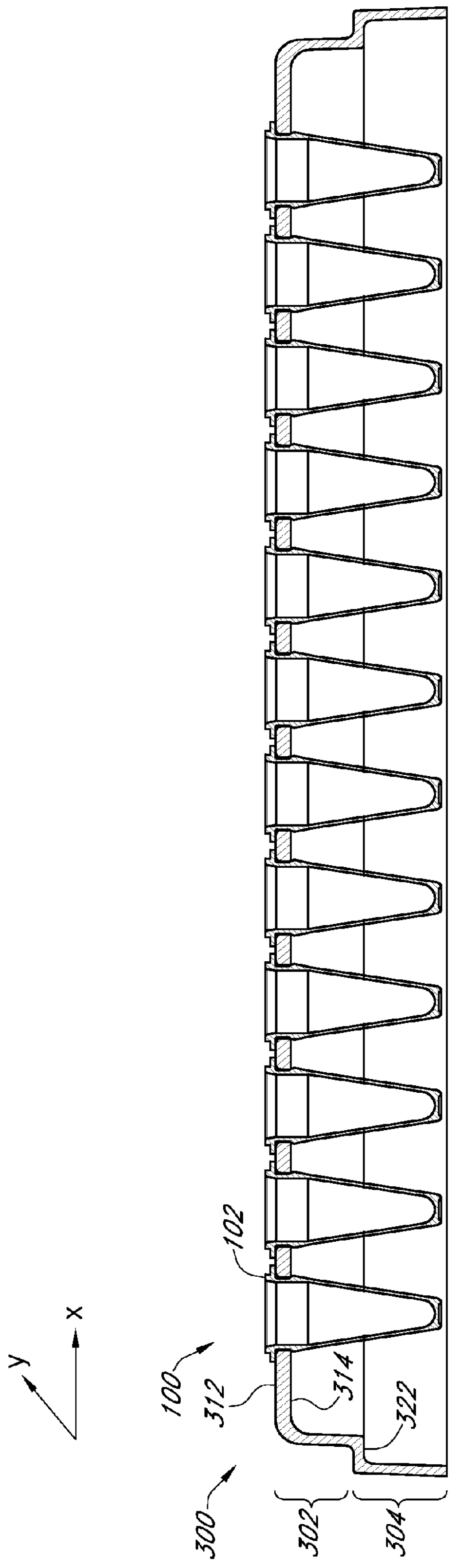
FIG. 6A is a cross-sectional view, taken along line 6A in FIG. 3B, of the 12 process tubes of FIG. 4 after securing the process tubes in the carrier tray.
Figure 6B:
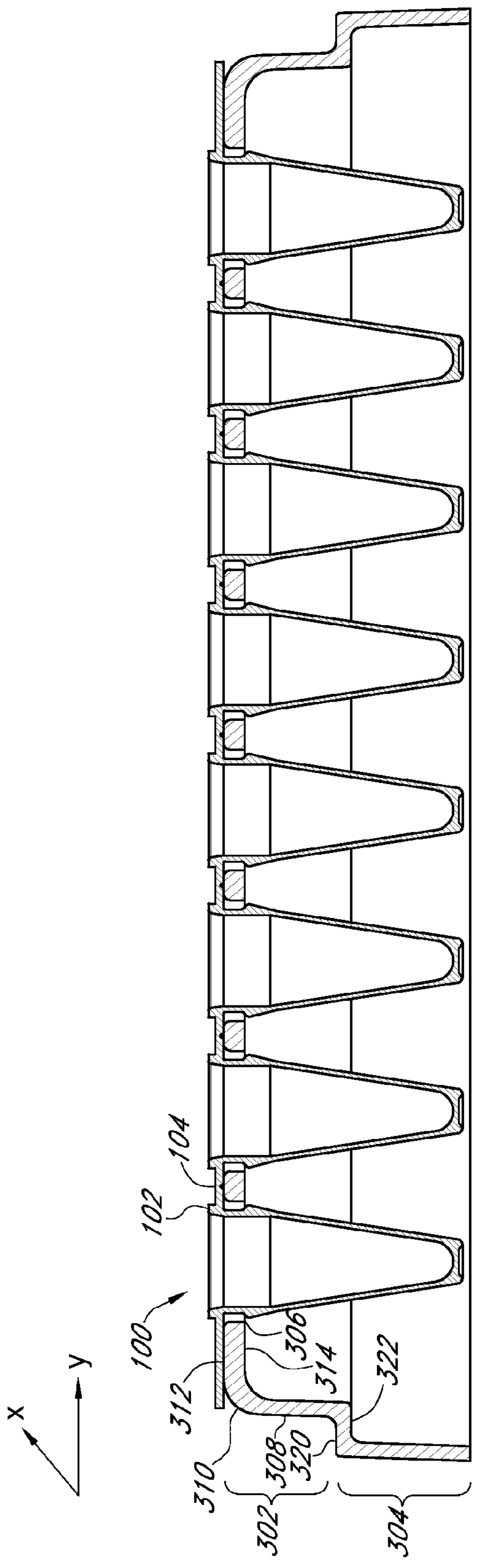
FIG. 6B is a cross-sectional view, taken along line 6B in FIG. 3B, of a process tube strip positioned in the carrier tray after securing the process tubes in the carrier tray.

FIG. 6A is a cross-sectional view, taken along line 6A in FIG. 3B, of the 12 process tubes 102 shown in FIG. 4. FIG. 6A shows the process tubes 102 now secured in the carrier tray 300. The direction of cross-section 6A in FIG. 3B provides a view of 12 process tubes 102, each from a different process tube strip 100. FIG. 6B is a cross-sectional view, taken along line 6B in FIG. 3B, of an entire process tube strip 100 positioned in the carrier tray 300 after securing the process tubes 102 in the carrier tray 300. As shown in FIG. 6B, the cross-sectional diameter of the elliptical port 306 in the y direction can be larger than the diameter of the protrusion 212.

Figure 7:
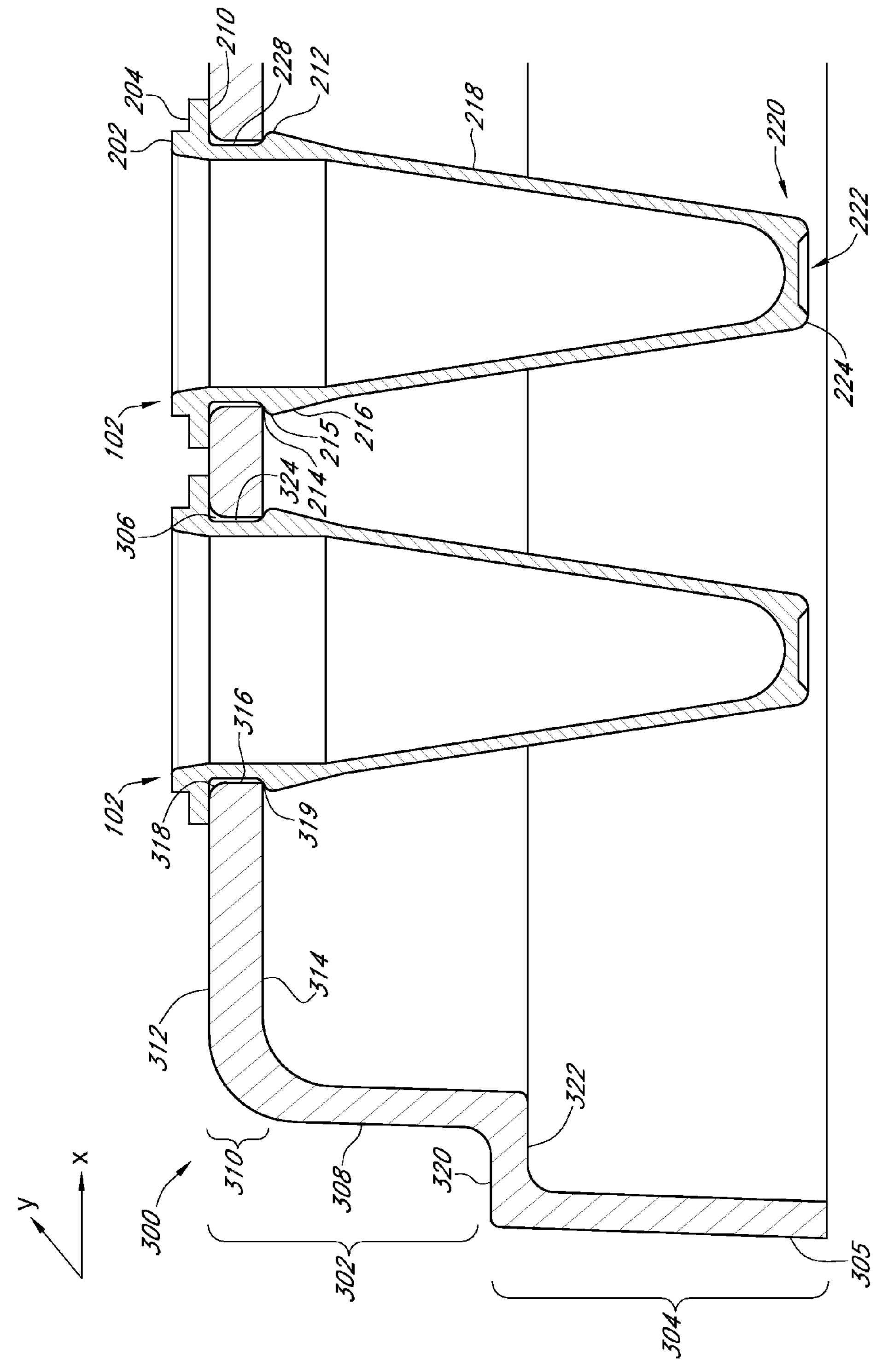
FIG. 7 is a cross-sectional view of the process tubes of FIG. 5 positioned in the carrier tray after securing the process tubes in the carrier tray.

FIG. 7 is a close-up view of two of the process tubes 102 shown in FIG. 6A and corresponds to the process tubes 102 of FIG. 5 after securing the process tubes 102 in the carrier tray 300. As shown in FIG. 7, the cross-sectional diameter of the elliptical port in the x direction can be smaller than the diameter of the protrusion 212. When the apex 215 of the protrusion 212 breaches the bottom edge 319, the upper slope 214 of the protrusion 212 comes into contact with, and lodges against, the bottom edge 319 of the port 306, at the bottom of the securement region 200. Also, when the apex 215 breaches the bottom edge 319, the lower surface 210 of the annular ledge 204 comes into contact with, and lodges against, the shelf top exterior 312 of the shelf 302, at the top of the securement region 200. At the top of the securement region 200, the annular ledge 204 is sufficiently wide at at least two points around the port 306 that the annular ledge 204 cannot pass through the port 306. In one embodiment, the annular ledge 204 can have a sufficiently large diameter to cover all points around the port 306. For example, the annular ledge 204 can have a larger diameter than the width and length diameters of the port 306. The height of the securement region 200 (from the lower surface 210 of the annular ledge 204 to a location on the upper slope 214 of the protrusion 212) corresponds approximately to the height of the port 306, between the port top edge 318 and the port bottom edge 319.

As shown in FIG. 7, the neck 228 of the process tube 102 can have a smaller outside diameter than the diameter of the port 306, creating a gap 324 between the process tube 102 and the port interior wall 314. In one embodiment, the outside diameter of the neck 228 can be a fixed circular diameter. As the port 306 can be elliptical in shape and have a larger length diameter on one side and a smaller width diameter on the other side, the width of the gap 324 can vary between the length side (y direction) and width side (x direction) of the port 306. For example, the size of the gap 324 on each length side of the port 306 can be approximately twice the size of the gap on each width side of the port 306.

The gap 324 provides a point of adjustment for the process tube 102 in the securement region 200. The gap 324 exists primarily between the neck 228 of the process tube 102 and the port interior wall 316, but the gap 324 also exists along a portion of the upper slope 214 of the protrusion 212 and along a portion of the lower surface 210 of the annular ledge 204. The gap 324 is enlarged slightly at the top portion of the securement region 200 because the rounded corners of the port top edge 318 provide additional distance between the port 306 and the neck 228 of the process tube 102. The gap 324 can provide the process tube 102 some degree of freedom of movement within the port 306 of the carrier tray 300, even when the process tube 102 is secured in the port 306.

The process tube 102 can be adjusted in the port 306 while being maintained securely in the port 306 because the point of contact between the upper slope 214 of the protrusion 212 and the port bottom edge 319 can adjust as the process tube 102 needs to tilt. When a process tube 102 tilts, the locations of the points of contact between the securement region 200 of the process tube 102 and the port 306 of the carrier tray 300 will adjust. For example, when the process tube tilts to one side, a point of contact on one side of the process tube 102 between the upper slope 214 and port bottom edge 319 moves near the top of the upper slope 214; on the other side of the tube, another point of contact moves to be near the bottom of the upper slope 214 (near the apex 215). Similar adjustment is possible at the top of the securement region 200, such that the neck 228 can be tilted towards the rounded port top edge 318 on one side of the process tube 102 and can be tilted away from the port top edge 318 on the other side of the process tube 102.

The gap 324 allows the process tube 102 to adjust when placing a plurality of process tubes into the carrier tray 100 as part of a process tube strip 100. Because of possible manufacturing variations of the carrier trays 300 and the process tubes 102, each carrier tray 300 may be sized slightly differently and each process tube 102 may fit in the carrier trays 300 differently. Given that the process tubes 102 are often attached together as part of a process tube strip 102 when inserted in the carrier tray 300, it is possible that, without mitigating considerations, the manufacturing variations of the carrier tray 300 and process tubes 102 could prevent accurate placement of an entire process tube strip 100 in a carrier tray 300. For example, accurate insertion of a process tube 102 at one end of a process tube strip 100 into the carrier tray 300 could prevent accurate insertion of the process tubes 102 at the other end of the process tube strip 100 into the carrier tray 300 because the process tubes 102 could be misaligned in either the x direction (lateral) or y direction (front to back). Even if a rigid process tube strip 100 is forced into the ports 306 of a carrier tray 300 despite being misaligned, the rigid attachment of the process tubes 102 would prevent the process tubes 102 from lying flat on the carrier tray 300 which could inhibit the hot stamping process.

The present disclosure addresses these issues in a number of ways, including allowing the process tubes 102 to tilt and adjust in the port 306 when the process tube strip 100 is being maneuvered and inserted in the carrier tray 300. The process tubes 102 can tilt and adjust in the port 306 because the gaps 324 allow for such motion. The elliptical shape of the ports 306 also enhances the adjustment available in the y direction. Also, the connector tabs 104 connecting the process tubes 102 are thin and pliable enough to allow maneuverability and adjustment between the individual process tubes 102 when inserting them in the carrier tray 300. In addition, the connector recess 232 (seen in FIG. 2B) on the connector tab 104 allows increased flexibility between the individual process tubes 102 when inserting them in the ports 306. In this manner, the gaps 324, the elliptical-shaped ports 306, and the connector tabs 104 afford the process tube 102 the capacity to adjust and always lay flat on the carrier tray 300 when inserting a process tube strip 100 into the carrier tray 300. Furthermore, the capacity of a process tube 102 to tilt or adjust in the carrier tray 300 facilities insertion of the process tube 102 into a heater of the thermal cycler, as discussed below in more detail.

When the process tubes 102 are secured in the ports 306 of the carrier tray 300, the process tubes 102 can undergo processing in preparation for use in a thermal cycler. Liquid reagents can be inputted into the secured process tubes 102. The process tubes 102 in the carrier tray 300 can be subjected to heat or other processes for drying or lyophilization in order to dry the liquid reagents in the process tubes 102. While secured in the carrier tray 300, the process tubes 102 can also be hot stamped to mark the process tubes 102, indicating the type of reagents added to the process tubes 102. The hot stamping can be in the form of a color stamped on the top ring 202 and/or the annular ledge 204.

The process of applying force to securing the process tubes 102 in the ports 306 of the carrier tray 300, the process of inputting liquid reagents into the secured process tubes 102, the process of drying the liquid reagents in the process tubes 102, and the process of hot stamping the process tubes 102 in carrier tray 300 can all be automated and performed at the site of manufacture and assembly of the process tubes 102 and carrier trays 300. The assembled carrier trays 300 containing the prepared process tubes 102 can then be shipped to the end user for additional processing such as depositing extracted nucleic acid samples in the process tubes 102 prior to running amplification assays on the samples the process tubes 102 in a thermal cycler. The addition of the extracted nucleic acid samples to the process tubes 102 acts to reconstitute the dried reagents to allow the reagents to associate with the nucleic acid samples in the reconstituted solution.

As described above, an end user can remove one or more process tube strips 100 from a single-color carrier tray 300 and exchange them with differently colored process tube strips 100 in a different carrier tray 300 to achieve the desired number and type of reagents for a given amplification assay. The force necessary to remove the process tube strip 100 can be approximately half of the force required to insert it. In one embodiment, the insertion force for a process tube strip 100 can have a range of approximately 0.7 lbs. force to 1.7 lbs. force and the removal force for the process tube strip 100 can have a range of approximately 0.3 lbs. force to 0.8 lbs force. In one embodiment, the insertion force for a process tube strip 100 can be approximately 1 lb. force and the removal force for the process tube strip 100 can be approximately 0.5 lb. force. In one embodiment, the force necessary to secure a process tube strip 100 in the ports 306 can be approximately 1.18 lbs. force and the force necessary to remove the process tube strip is 0.60 lbs. force. The insertion and removal forces prescribed for the process tube strips 100 insure that a process tube strip 100 is not overly difficult to insert or remove from the carrier tray 300 and also prevent the process tube strips 100 from falling out of the carrier tray under normal handling conditions.

It is of note that the same carrier tray 300 (housing the process tubes 102) in which the mixing of reagents and nucleic acid samples occurs can be input directly into the thermal cycler. Thus, the end user is not required to do the mixing of reagents and nucleic acid in one tube and then transport that mixed solution to another tube, or even move the first tube to another tray. In the present disclosure, the process tubes 102 containing the reagents and secured in the carrier tray 300 can receive the samples, e.g., nucleic acid samples, and, then without removing the process tubes 102 from the carrier tray 300, can be input into the thermal cycler for amplification assays.

It is also contemplated that solid reagents may be added to the process tubes 102 in addition to, or instead of, the liquid reagents. It is also contemplated that empty process tubes 102 and carrier trays 300 can be supplied to the end user and the end user can deposit the solid or liquid reagents in the process tubes 102 prior to adding the nucleic acid samples.

The securement force, the force necessary to push the process tube 102 securely into the port 306, can be applied simultaneously to multiple (or all) process tubes 102 in the carrier tray 300. Alternatively, the securement force can be applied separately to individual process tubes 102 one at a time, as needed. The securement force can be applied in an automated manner and can be conducted concurrently along with the automated steps of filling the process tubes 102 with reagents and hot stamping the process tubes 102. In some instances, the same apparatus can be used to hot stamp and apply the securement force to the process tubes 102. Alternatively, separate apparatuses can be used for hot stamping and applying the securement force.

When a separate securement force device and a hot stamping device are used, the securement force can first be applied to secure the process tubes 102 in the ports 306 of the carrier tray 300 prior to hot stamping the top ring 202 of the process tubes 102. In some instances, the automated hot stamping apparatus may stick to the top ring 202 of the process tubes 102 when applying pressure to the top ring 202. Because of the novel way in which the process tubes 102 are secured in the carrier tray 300 in the embodiments described herein, a process tubes 102 are not pulled up and out of the carrier tray 300 when the hot stamping apparatus pulls apart from the process tube 102 being stamped. Furthermore, because the process tubes 102 are secured in the carrier tray 300, the process tubes 102 can be transported without risk of the process tubes 102 falling out of the carrier tray 300. The embodiments disclosed herein also advantageously overcome other issues that present in other PCR tube trays, such as bunching of tubes on one side of the tray or tubes falling out of alignment in the tray.

Figure 8:
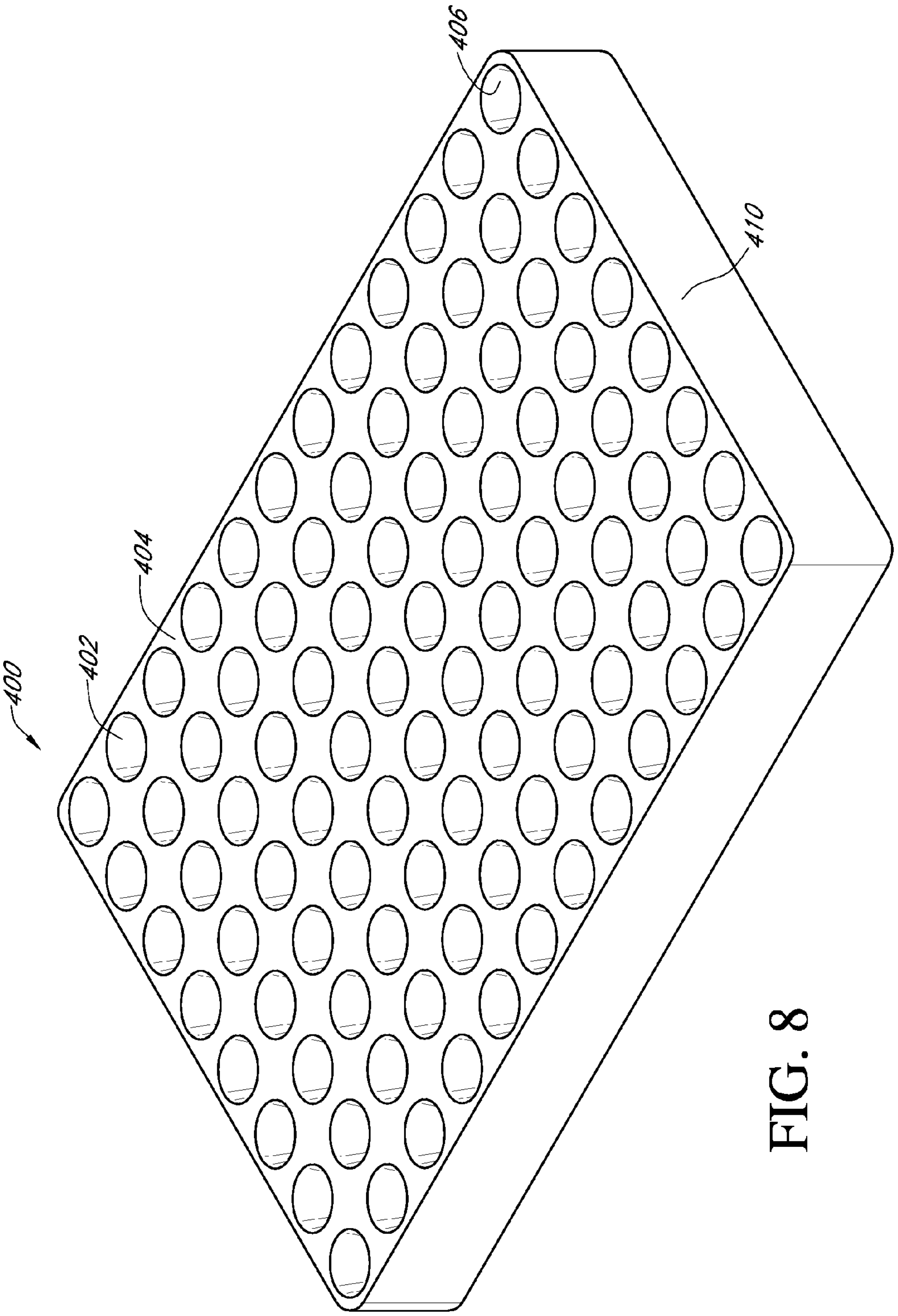
FIG. 8 is an isometric view of an exemplary heater assembly of a thermal cycler.

FIG. 8 is an isometric view of an exemplary heater assembly 400 to be used in a thermal cycler (not shown). Amplification assays (such as PCR or isothermal amplification) can be performed in the thermal cycler. The heater assembly 400 is part of temperature cycling-subsystem of the thermal cycler and can work in conjunction with other subsystems of the thermal cycler, such as a detection subsystem. The exemplary heater assembly 400 shown in FIG. 8 is a 96-well assembly containing 96 heater wells 402, although other assemblies are contemplated (e.g., 48-well assemblies, etc.). The heater assembly 400 includes a flat top surface 404 between the heater wells 402, and a side surface 410. Each heater well 402 is conical in shape and is comprised of an interior wall 406 and a well bottom 412. The heater wells 402 in the heater assembly 400 are arranged in an array of 8 rows and 12 columns to correspond to the spatial arrangement of process tubes 102 in a carrier tray 300.

Each heater well 402 can receive a process tube 102. The carrier tray 300 can be placed directly over the heater assembly 400 in the thermal cycler in order to place all process tube 102 in the carrier tray 300 into the heater assembly 400 simultaneously. Not shown in FIG. 8 is the casing around the heater assembly 400 or the necessary circuitry to provide heat to the heater wells 402.

Because of possible manufacturing variations of the carrier trays 300 and the process tubes 102, each carrier tray 300 may be sized slightly differently and each process tube 102 may fit in the carrier trays 300 differently. If the process tubes 102 were rigidly attached to the carrier tray 300, the manufacturing tolerances could prevent all of the process tubes in a 96-tube carrier tray 300 from accurately being placed in the heater wells 402. For example, fitting a process tube 102 in a heater well 402 on one side of the heater assembly 400 may prevent a process tube 102 on the other side of the heater assembly 400 from being accurately and securely placed into its respective heater well 402. As described above, the process tubes 102 are able to float or adjust slightly when secured in the carrier tray 300 because of the gap 324 between the port interior wall 316 and the securement region 200 of the process tube 102. The connector recess 232 (seen in FIG. 2B) on the connector tab 104 also allows flexibility between the individual process tubes 102 when inserting them in the heater wells 402. Allowing the process tubes 102 to float within ports 306 of the carrier tray 300 permits the process tubes 102 to adjust position to fit accurately and securely into the heater wells 402 of the heater assembly 400.

Figure 9:
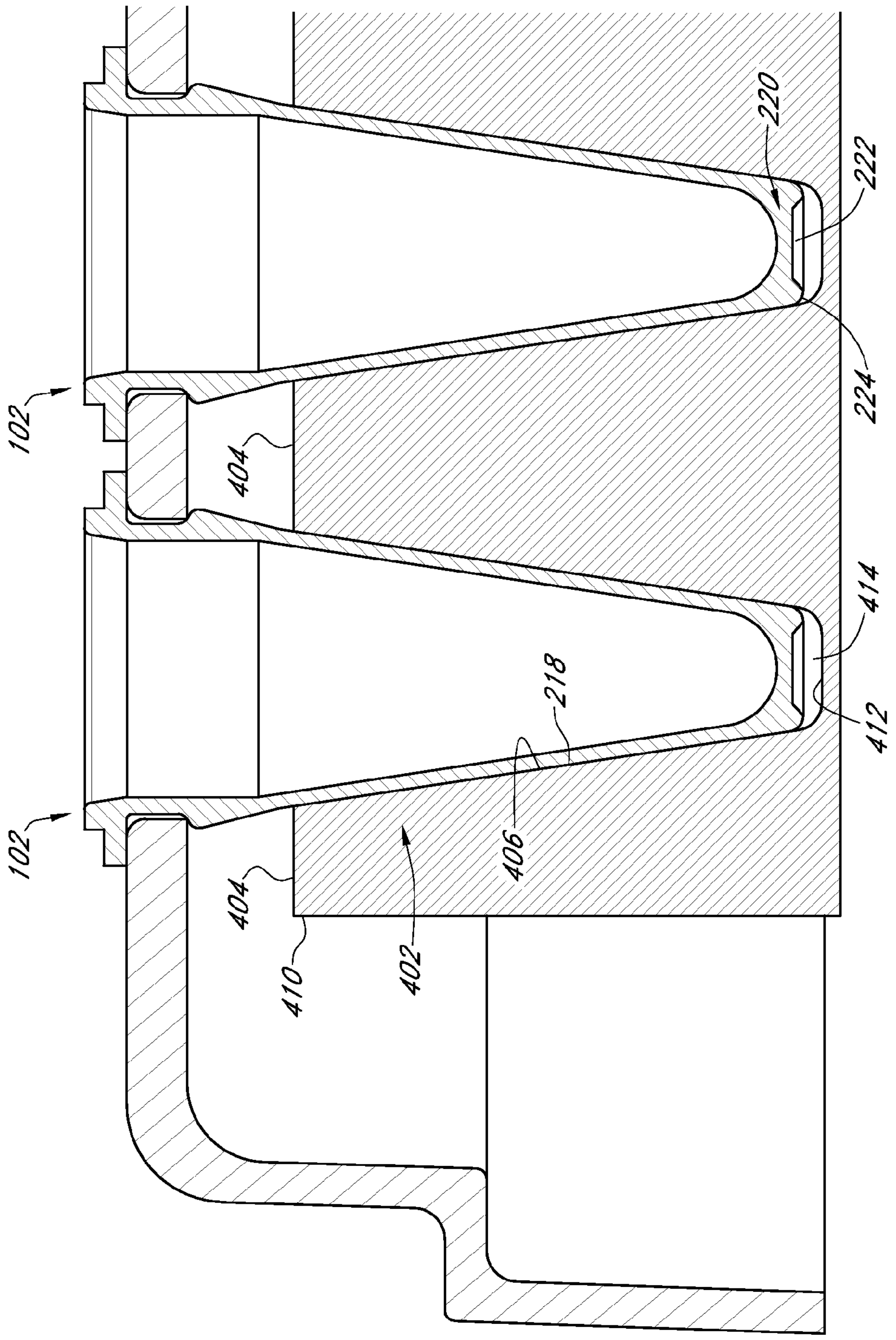
FIG. 9 is a cross-sectional view of exemplary process tubes positioned in heater wells of a heater assembly, as described herein.

FIG. 9 is a cross-sectional view of two exemplary process tubes 102 positioned in heater wells 402 of the heater assembly 400. When the process tube 102 is placed in the heater well 402, the body 218 of the process tube 102 comes in physical contact with, and is mated to, the interior wall 406 of the heater well 402. In some embodiments, the heater well 402 is deeper than the body 218 of the process tube 102, such that when the process tube 102 is secured in a port 306 of the carrier tray 300 and the carrier tray 300 is positioned over the heater assembly 400, the base 220 of the process tube 102 does not extend to the well bottom 412. In this manner, a gap 414 is created between the base 220 of the process tube 102 and the well bottom 412. The gap 414 ensures that the body 218 of the process tube 102 remain in physical contact with the well interior wall 406; if the base 220 of the process tube 102 were to bottom out in the heater well bottom 412 first, before the body 218 contacts the well interior wall 406, a gap could exist between the wall 406 and the body 218 of the process tube 102 and cause poor heat transfer between the heater well 402 and the process tube 102. Thus, the gap 414 below the process tube 102 ensures that a gap does not exist between the wall 406 and the body 218 of the process tube 102. The heater well 402 can surround the body 218 of the process tube 102 and provide uniform heating to the contents of the process tube 102 during the thermal cycling steps of the amplification assay. When the process tube 102 is placed in the heater well 402, the heater well 402 can surround the body 218 of the process tube to a location just below the lower slope 216 of the protrusion 212.

The above description discloses multiple methods and systems of the embodiments disclosed herein. The embodiments disclosed herein are susceptible to modifications in the methods and materials, as well as alterations in the fabrication methods and equipment. Such modifications will become apparent to those skilled in the art from a consideration of this disclosure or practice of the invention disclosed herein. Consequently, it is not intended that the embodiments disclosed herein be limited to the specific embodiments disclosed herein, but that it cover all modifications and alternatives coming within the true scope and spirit of the invention.

Example 1

This example illustrates a specific process for preparing a carrier tray 300 with process tubes 102 to be provided to an end user.

1. Manufacturing 12 process tube strips containing eight connected process tubes formed from polypropylene.
2. Manufacturing a carrier tray from polycarbonate having 96 ports in an 8×12 array.
3. The 12 process tube strips are placed in the carrier tray.
4. The process tubes of the process tube strips are secured in the ports of the carrier tray by applying a force to the top ring of the process tube.
5. Each process tube in the carrier tray is filled with the same specific liquid reagents.
6. The carrier tray is heated to dry the reagents in the process tubes.
7. The process tubes are hot stamped with specific colors to indicate the assay for which they will be used.
8. The carrier tray is stacked and packaged with other carrier trays having the same or different reagents and shipped to the end user.
9. The end user can use the entire carrier tray as is, or may depopulate the carrier tray and repopulate the carrier tray or trays with a mix of individual process tube strips or tubes of various reagent types.

Example 2

This example describes the test procedure and results of a test to determine the force necessary to secure the process tube strips 100 in the ports 306 of the carrier tray 300 and the force necessary to subsequently remove the process tube strips 100 from the ports 306.

An Amtek AccuForce Cadet Force Gage, (0-5 lbs) was used to measure the force necessary to secure and remove the process tubes 102 in the ports 306.

Test Procedure

1. Lay one strip of tubes in a column of the carrier tray. (Not yet secured in the carrier tray)
2. Turn on the gage.
3. Zero the gage with the gage in the upright position.
4. Clear the gage.
5. Slowly press down on each tube within the strip starting at the "A" row with the gage at a slight angle ~2-3 degrees from vertical on each tube until all the tubes snap into place.
6. Record the force value on the gauge and the column number as insertion values.
7. Press the clear button to clear the memory.
8. Lay the second strip of tubes in the second column. Repeat steps 5-7.
9. Repeat steps 5-7 for the remaining strips 3-12.

10. Turn the carrier tray upside down and starting with the first strip slowly press the tubes out of the carrier starting at the “A” row.
11. Record the force value and the column number as removal values.
12. Press the clear button to clear the memory.
13. Repeat steps 10, 11 and 12 for the remaining process tube strips.
14. Rearrange the 12 process tube strips in the carrier tray and repeat steps 3-13.

Results

The results of the force testing are provided in Table 1. Table 1 shows the force necessary to insert and secure all the process tubes 102 of a process tube strip 100 in a carrier tray 300. As shown, the average insertion force to secure the process tube strips 100 in the carrier tray 300 was 1.18 lbs force and the average removal force was 0.60 lbs force.

TABLE 1

| Process Tube Insertion and Removal Testing | | | | | | | | | |
|---|---|---|---|---|---|---|---|---|---|
| | Tube Strips | | | | | | | | |
| 1$^{st}$ Round | 1 | 2 | 3 | 4 | 5 | 6 | | | |
| Insertion | 0.708 | 1.084 | 1.137 | 1.467 | 0.945 | 1.476 | | | |
| Removal | 0.313 | 0.478 | 0.573 | 0.589 | 0.520 | 0.518 | | | |
| 1$^{st}$ Round | 7 | 8 | 9 | 10 | 11 | 12 | Avg | | |
| Insertion | 0.866 | 1.075 | 1.408 | 0.969 | 1.025 | 1.217 | 1.115 | | |
| Removal | 0.553 | 0.978 | 0.767 | 0.388 | 0.602 | 0.485 | 0.564 | | |
| 2$^{nd}$ Round - tube strips randomly rearranged | | | | | | | | | |
| | 1 | 2 | 3 | 4 | 5 | 6 | | | |
| Insertion | 0.668 | 0.904 | 1.661 | 1.727 | 1.677 | 1.296 | | | |
| Removal | 0.439 | 0.534 | 0.699 | 0.630 | 0.584 | 0.652 | | | |
| | 7 | 8 | 9 | 10 | 11 | 12 | Avg | | |
| Insertion | 1.536 | 1.051 | 1.280 | 1.056 | 1.012 | 0.983 | 1.238 | Average Insertion | 1.18 |
| Removal | 0.723 | 0.675 | 0.778 | 0.750 | 0.619 | 0.514 | 0.633 | Average Removal | 0.60 |

What is claimed is:

1. A system comprising:

a carrier tray comprising a plurality of elliptical ports therethrough, each port having a top edge, a bottom edge, an interior wall, and a length diameter that is larger than a width diameter;

a process tube comprising a securement region on the exterior of the tube, the securement region comprising an annular ledge, an annular protrusion, and a neck between the ledge and the protrusion, wherein the protrusion comprises an apex, an upper slope from the apex to the neck, and a lower slope from the apex to the body, wherein the angle of the upper slope on the protrusion is steeper than the angle of the lower slope on the protrusion, wherein the process tube securely fits in an elliptical port of the plurality of elliptical ports of the carrier tray such that a bottom surface of the ledge rests on a top surface of the carrier tray and the upper slope of the protrusion contacts the bottom edge of the port, wherein a diameter of the neck is less than the length diameter and the width diameter of the port, wherein a diameter of the protrusion at the apex is larger than the width diameter of the port, and wherein a cross-section of the process tube is circular; and a heater assembly comprising a plurality of heater wells, each heater well comprising an inner wall and a well bottom, wherein the process tube is received in a heater well of the plurality of heater wells such that the body of the process tube contacts the inner wall of the heater well and a gap is formed between a base of the process tube and the well bottom of the heater well, the gap configured to prevent the process tube from bottoming out in the heater well.

2. The system of claim 1, wherein the annular ledge of the process tube has an outside diameter that is larger than the length and width diameters of the ports of the carrier tray and the neck of the process tube has an outside diameter that is smaller than the length and width diameters of the port.

3. The system of claim 1, wherein the protrusion of the process tube has an outside diameter that is larger than at least the width diameter of the port.

4. The system of claim 1, wherein the process tube is configured to tilt within the port of the carrier tray.

5. The system of claim 1, further comprising a plurality of process tubes connected together as a process tube strip, each process tube securely fit within a separate port of the carrier tray.

6. The system of claim 5, wherein the plurality of process tubes in the process tube strip are connected by a connector tab extending between the annular ledges of adjacent process tubes.

7. The system of claim 6, wherein the connector tab comprises a connector recess on the underside thereof.

8. The system of claim 5, wherein the force necessary to remove the process tube strip from the carrier is approximately half of the force required to insert the process tube strip in the carrier.

9. The system of claim 1, wherein the apex of the protrusion of the process tube is circular having a constant outside diameter.

10. The system of claim 1, wherein an outside diameter of the neck of the process tube is a fixed circular diameter.

11. The system of claim 1, wherein the protrusion of the process tube is annular extending laterally from the exterior of the process tube.

12. The system of claim 1, wherein the heater well surrounds the body of the process tube to a location just below the lower slope of the protrusion.

13. The system of claim 1, wherein the inner wall of the heater well is conical and the body of the process tube is conical.

14. The system of claim 1, wherein the diameter of the neck is less than the length diameter and the width diameter of the port such that the process tube can be adjusted within the elliptical port so as to fit accurately and securely into the heater well.

* * * * *